(12) United States Patent
Nakada et al.

(10) Patent No.: US 12,269,895 B2
(45) Date of Patent: Apr. 8, 2025

(54) METHOD FOR IMPROVING AFFINITY OF ANTIBODY FOR ANTIGEN AND USE THEREOF

(71) Applicant: SYSMEX CORPORATION, Kobe (JP)

(72) Inventors: Tomofumi Nakada, Kobe (JP); Yuriko Egashira, Kobe (JP); Atsushi Fukunaga, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 160 days.

(21) Appl. No.: 17/645,619

(22) Filed: Dec. 22, 2021

(65) Prior Publication Data

US 2022/0204649 A1 Jun. 30, 2022

(30) Foreign Application Priority Data

Dec. 25, 2020 (JP) .................... 2020-217336

(51) Int. Cl.
| | |
|---|---|
| *C12P 21/06* | (2006.01) |
| *C07K 16/00* | (2006.01) |
| *C07K 16/26* | (2006.01) |
| *C07K 16/28* | (2006.01) |
| *C07K 16/32* | (2006.01) |
| *C07K 16/40* | (2006.01) |

(52) U.S. Cl.
CPC .............. *C07K 16/40* (2013.01); *C07K 16/00* (2013.01); *C07K 16/26* (2013.01); *C07K 16/2863* (2013.01); *C07K 16/32* (2013.01); *C07K 2317/55* (2013.01); *C07K 2317/567* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 2013/0143245 A1 | 6/2013 | Fukunaga |
| 2018/0179298 A1 | 6/2018 | Maeta et al. |
| 2021/0230298 A1 | 7/2021 | Maeta et al. |
| 2021/0230304 A1 | 7/2021 | Maeta et al. |
| 2021/0230305 A1 | 7/2021 | Maeta et al. |
| 2021/0230306 A1 | 7/2021 | Maeta et al. |
| 2021/0230307 A1 | 7/2021 | Maeta et al. |
| 2021/0261687 A1 | 8/2021 | Maeta et al. |

FOREIGN PATENT DOCUMENTS

| JP | 5528643 B2 | 6/2014 |
| JP | 2018-108072 A | 7/2018 |
| WO | 2013/084371 A1 | 6/2013 |

OTHER PUBLICATIONS

Atsushi Fukunaga et al., "Improving the affinity of an antibody for its antigen via long-range electrostatic interactions", Protein Engineering, Design & Selection, 2013, pp. 773-780, vol. 26, No. 12.
Cyrus Chothia et al., "Canonical Structures for the Hypervariable Regions of Immunoglobulins", J. Mol. 1987, pp. 901-917, vol. 196.
Marie-Paule Lefranc et al. "IMGT unique numbering for immunoglobulin and T cell receptor constant domains and Ig superfamily C-like domains", Developmental and Comparative Immunology, 2005, pp. 185-203, vol. 29.
Annemarie Honegger et al., "Yet Another Numbering Scheme for Immunoglobulin Variable Domains: An Automatic Modeling and Analysis Tool", J. Mol. Biol. 2001, pp. 657-670, vol. 309.
G. Köhler et al., "Continuous cultures of fused cells secreting antibody of predefined specificity", The Journal of Immunology, Aug. 7, 1975, pp. 495-497, vol. 256.
Atsushi Fukunaga et al., "Improvement of antibody affinity by introduction of basic amino acid residues into the framework region", Biochemistry and Biophysics Reports, 2018, pp. 81-85, vol. 15.
Extended European Search Report, dated May 23, 2022, issued by the European Patent Office in European Application No. 21217221.7.
Communication issued Dec. 17, 2024 in Japanese Application No. 2020-217336.

*Primary Examiner* — Chun W Dahle
(74) *Attorney, Agent, or Firm* — Sughrue Mion, PLLC

(57) ABSTRACT

Disclosed is a method for improving affinity of an antibody for an antigen, the method comprising: in the antibody, changing at least 3 amino acid residues of framework region 3 (FR3) as defined by Kabat method to arginine residues or lysine residues, thereby improving affinity of an antibody for an antigen as compared with that of an antibody before said at least 3 amino acid residues are changed to arginine residues or lysine residues, wherein said at least 3 amino acid residues comprise at least 3 selected from the group consisting of amino acid residues at positions 68, 70, 72, 74, 75, 77, 79, 81, 82A, 82B, 83, 84, 85 and 87 of a heavy chain as defined by the Kabat method.

20 Claims, 4 Drawing Sheets

Specification includes a Sequence Listing.

FIG. 6A

DIQMTQSPSSLSASVGDRVTITCRASQDVNTAVAWYQQKPGKAPKLLIYSASFLYSGVPSRFSGSRSG
TDFTLTISSLQPEDFATYYCQQHYTTPPTFGQGTKVEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSSP
VTKSFNRGEC

FIG. 6B

EVQLVESGGGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK

FIG. 6C

EVQLVESGGGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSC

```
SEQUENCE LISTING

<160> NUMBER OF SEQ ID NOS: 25

<210> SEQ ID NO 1
<211> LENGTH: 214
<212> TYPE: PRT
<213> ORGANISM: Artificial Sequence
<220> FEATURE:
<223> OTHER INFORMATION: Synthetic sequence, humanized antibody

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 2
<211> LENGTH: 450
<212> TYPE: PRT
<213> ORGANISM: Artificial Sequence
<220> FEATURE:
<223> OTHER INFORMATION: Synthetic sequence, humanized antibody

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 3
<211> LENGTH: 223
<212> TYPE: PRT
<213> ORGANISM: Artificial Sequence
<220> FEATURE:
<223> OTHER INFORMATION: Synthetic sequence, humanized antibody

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 4
<211> LENGTH: 11

```
<212> TYPE: PRT
<213> ORGANISM: Artificial Sequence
<220> FEATURE:
<223> OTHER INFORMATION: Synthetic sequence, humanized antibody

<400> SEQUENCE: 4

Arg Ala Ser Gln Asp Val Asn Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence, humanized antibody

<400> SEQUENCE: 5

Ser Ala Ser Phe Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic sequence, humanized antibody

<400> SEQUENCE: 6

Gln Gln His Tyr Thr Thr Pro Pro Thr
1               5

<210> SEQ ID NO 7
<211> LENGTH: 110
<212> TYPE: PRT
<213> ORGANISM: Artificial Sequence
<220> FEATURE:
<223> OTHER INFORMATION: Synthetic sequence, humanized antibody

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val
            100                 105                 110

<210> SEQ ID NO 8
<211> LENGTH: 5
<212> TYPE: PRT
<213> ORGANISM: Artificial Sequence
<220> FEATURE:
<223> OTHER INFORMATION: Synthetic sequence, humanized antibody

<400> SEQUENCE: 8

Asp Thr Tyr Ile His
1               5
```

<210> SEQ ID NO 9
<211> LENGTH: 17
<212> TYPE: PRT
<213> ORGANISM: Artificial Sequence
<220> FEATURE:
<223> OTHER INFORMATION: Synthetic sequence, humanized antibody

<400> SEQUENCE: 9

Arg Ile Tyr Pro Thr Asn Gly Tyr Thr Arg Tyr Ala Asp Ser Val Lys
1               5                   10                  15

Gly

<210> SEQ ID NO 10
<211> LENGTH: 11
<212> TYPE: PRT
<213> ORGANISM: Artificial Sequence
<220> FEATURE:
<223> OTHER INFORMATION: Synthetic sequence, humanized antibody

<400> SEQUENCE: 10

Trp Gly Gly Asp Gly Phe Tyr Ala Met Asp Tyr
1               5                   10

<210> SEQ ID NO 11
<211> LENGTH: 120
<212> TYPE: PRT
<213> ORGANISM: Artificial Sequence
<220> FEATURE:
<223> OTHER INFORMATION: Synthetic sequence, humanized antibody

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 12
<211> LENGTH: 214
<212> TYPE: PRT
<213> ORGANISM: Mus musculus

<400> SEQUENCE: 12

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Ile
        35                  40                  45

```
Lys Tyr Ala Ser Gln Ser Ile Ser Gly Ile Pro Ser Arg Phe Ser Gly
             50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Tyr
                 85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 13
<211> LENGTH: 231
<212> TYPE: PRT
<213> ORGANISM: Mus musculus

<400> SEQUENCE: 13

Asp Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Ser Asp
             20                  25                  30

Tyr Trp Ser Trp Ile Arg Lys Phe Pro Gly Asn Arg Leu Glu Tyr Met
         35                  40                  45

Gly Tyr Val Ser Tyr Ser Gly Ser Thr Tyr Tyr Asn Pro Ser Leu Lys
     50                  55                  60

Ser Arg Ile Ser Ile Thr Arg Asp Thr Ser Lys Asn Gln Tyr Tyr Leu
 65                  70                  75                  80

Asp Leu Asn Ser Val Thr Thr Glu Asp Thr Ala Thr Tyr Tyr Cys Ala
                 85                  90                  95

Asn Trp Asp Gly Asp Tyr Trp Gly Gln Gly Thr Leu Val Thr Val Ser
                100                 105                 110

Ala Ala Lys Thr Thr Pro Pro Ser Val Tyr Pro Leu Ala Pro Gly Ser
            115                 120                 125

Ala Ala Gln Thr Asn Ser Met Val Thr Leu Gly Cys Leu Val Lys Gly
        130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
                180                 185                 190

Val Thr Cys Asn Val Ala His Pro Ala Ser Ser Thr Lys Val Asp Lys
```

```
                195                 200                 205
Lys Ile Val Pro Arg Asp Cys Gly Ser Lys Pro Ser Ile Cys Gly Gly
    210                 215                 220

Ser His His His His His
225                 230

<210> SEQ ID NO 14
<211> LENGTH: 231
<212> TYPE: PRT
<213> ORGANISM: Artificial Sequence
<220> FEATURE:
<223> OTHER INFORMATION: Synthetic sequence, modified antibody

<400> SEQUENCE: 14

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Asp
            20                  25                  30

Tyr Trp Ser Trp Ile Arg Lys Phe Pro Gly Asn Arg Leu Glu Tyr Met
        35                  40                  45

Gly Tyr Val Ser Tyr Ser Gly Ser Thr Tyr Tyr Asn Pro Ser Leu Lys
    50                  55                  60

Ser Arg Ile Arg Ile Arg Arg Thr Ser Lys Asn Gln Tyr Tyr Leu
65                  70                  75                  80

Asp Leu Asn Ser Val Thr Thr Glu Asp Thr Ala Thr Tyr Tyr Cys Ala
                85                  90                  95

Asn Trp Asp Gly Asp Tyr Trp Gly Gln Gly Thr Leu Val Thr Val Ser
            100                 105                 110

Ala Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Ser Lys Pro Ser Ile Cys Gly Gly
    210                 215                 220

Ser His His His His His
225                 230

<210> SEQ ID NO 15
<211> LENGTH: 231
<212> TYPE: PRT
<213> ORGANISM: Artificial Sequence
<220> FEATURE:
<223> OTHER INFORMATION: Synthetic sequence, modified antibody

<400> SEQUENCE: 15

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Asp
            20                  25                  30
```

Tyr Trp Ser Trp Ile Arg Lys Phe Pro Gly Asn Arg Leu Glu Tyr Met
            35                  40                  45

Gly Tyr Val Ser Tyr Ser Gly Ser Thr Tyr Tyr Asn Pro Ser Leu Lys
 50                  55                  60

Ser Arg Ile Ser Ile Thr Arg Asp Thr Ser Lys Asn Gln Tyr Arg Leu
 65                  70                  75                  80

Arg Leu Arg Ser Val Thr Thr Glu Asp Thr Ala Thr Tyr Tyr Cys Ala
                 85                  90                  95

Asn Trp Asp Gly Asp Tyr Trp Gly Gln Gly Thr Leu Val Thr Val Ser
                100                 105                 110

Ala Ala Lys Thr Thr Pro Pro Ser Val Tyr Pro Leu Ala Pro Gly Ser
            115                 120                 125

Ala Ala Gln Thr Asn Ser Met Val Thr Leu Gly Cys Leu Val Lys Gly
        130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Ser Lys Pro Ser Ile Cys Gly Gly
    210                 215                 220

Ser His His His His His His
225                 230

<210> SEQ ID NO 16
<211> LENGTH: 231
<212> TYPE: PRT
<213> ORGANISM: Artificial Sequence
<220> FEATURE:
<223> OTHER INFORMATION: Synthetic sequence, modified antibody

<400> SEQUENCE: 16

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Asp
            20                  25                  30

Tyr Trp Ser Trp Ile Arg Lys Phe Pro Gly Asn Arg Leu Glu Tyr Met
            35                  40                  45

Gly Tyr Val Ser Tyr Ser Gly Ser Thr Tyr Tyr Asn Pro Ser Leu Lys
 50                  55                  60

Ser Arg Ile Ser Ile Thr Arg Asp Thr Ser Lys Asn Gln Tyr Tyr Leu
 65                  70                  75                  80

Asp Leu Asn Arg Val Arg Arg Glu Asp Thr Ala Thr Tyr Tyr Cys Ala
                 85                  90                  95

Asn Trp Asp Gly Asp Tyr Trp Gly Gln Gly Thr Leu Val Thr Val Ser
                100                 105                 110

Ala Ala Lys Thr Thr Pro Pro Ser Val Tyr Pro Leu Ala Pro Gly Ser
            115                 120                 125

Ala Ala Gln Thr Asn Ser Met Val Thr Leu Gly Cys Leu Val Lys Gly
        130                 135                 140

Tyr Phe Pro Glu Pro Val Thr Val Thr Trp Asn Ser Gly Ser Leu Ser
145                 150                 155                 160

```
Ser Gly Val His Thr Phe Pro Ala Val Leu Gln Ser Asp Leu Tyr Thr
            165                 170                 175

Leu Ser Ser Ser Val Thr Val Pro Ser Ser Thr Trp Pro Ser Glu Thr
        180                 185                 190

Val Thr Cys Asn Val Ala His Pro Ala Ser Ser Thr Lys Val Asp Lys
        195                 200                 205

Lys Ile Val Pro Arg Asp Cys Gly Ser Lys Pro Ser Ile Cys Gly Gly
        210                 215                 220

Ser His His His His His
225                 230
```

<210> SEQ ID NO 17
<211> LENGTH: 214
<212> TYPE: PRT
<213> ORGANISM: Artificial Sequence
<220> FEATURE:
<223> OTHER INFORMATION: Synthetic sequence, humanized antibody

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 18
<211> LENGTH: 238
<212> TYPE: PRT
<213> ORGANISM: Artificial Sequence
<220> FEATURE:
<223> OTHER INFORMATION: Synthetic sequence, humanized antibody

<400> SEQUENCE: 18

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
210                 215                 220

Asp Lys Thr Gly Ser Cys Gly Gly His His His His His
225                 230                 235

<210> SEQ ID NO 19
<211> LENGTH: 238
<212> TYPE: PRT
<213> ORGANISM: Artificial Sequence
<220> FEATURE:
<223> OTHER INFORMATION: Synthetic sequence, modified antibody

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Arg Ile Arg Ala Arg Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Pro Lys Ser Cys
210                 215                 220

Asp Lys Thr Gly Ser Cys Gly Gly His His His His His
225                 230                 235
```

<210> SEQ ID NO 20
<211> LENGTH: 238
<212> TYPE: PRT
<213> ORGANISM: Artificial Sequence
<220> FEATURE:
<223> OTHER INFORMATION: Synthetic sequence, modified antibody

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Arg Thr Ser Lys Asn Arg Ala Arg
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Pro Lys Ser Cys
210                 215                 220

Asp Lys Thr Gly Ser Cys Gly Gly His His His His His
225                 230                 235
```

<210> SEQ ID NO 21
<211> LENGTH: 238
<212> TYPE: PRT
<213> ORGANISM: Artificial Sequence
<220> FEATURE:
<223> OTHER INFORMATION: Synthetic sequence, modified antibody

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Arg Arg Asn Arg Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220

Asp Lys Thr Gly Ser Cys Gly Gly His His His His His His
225                 230                 235
```

<210> SEQ ID NO 22
<211> LENGTH: 238
<212> TYPE: PRT
<213> ORGANISM: Artificial Sequence
<220> FEATURE:
<223> OTHER INFORMATION: Synthetic sequence, modified antibody

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Arg
65                  70                  75                  80

Leu Arg Met Arg Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
```

```
            100                 105                 110
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Pro Lys Ser Cys
        210                 215                 220

Asp Lys Thr Gly Ser Cys Gly Gly His His His His His His
225                 230                 235
```

<210> SEQ ID NO 23
<211> LENGTH: 238
<212> TYPE: PRT
<213> ORGANISM: Artificial Sequence
<220> FEATURE:
<223> OTHER INFORMATION: Synthetic sequence, modified antibody

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Arg Leu Arg Arg Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Pro Lys Ser Cys
        210                 215                 220

Asp Lys Thr Gly Ser Cys Gly Gly His His His His His His
```

```
<210> SEQ ID NO 24
<211> LENGTH: 238
<212> TYPE: PRT
<213> ORGANISM: Artificial Sequence
<220> FEATURE:
<223> OTHER INFORMATION: Synthetic sequence, modified antibody

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Arg Arg Asp Arg Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220

Asp Lys Thr Gly Ser Cys Gly Gly His His His His His His
225                 230                 235

<210> SEQ ID NO 25
<211> LENGTH: 10
<212> TYPE: PRT
<213> ORGANISM: Artificial Sequence
<220> FEATURE:
<223> OTHER INFORMATION: Synthetic sequence, His tag

<400> SEQUENCE: 25

Cys Gly Gly Ser His His His His His His
1               5                   10
```

METHOD FOR IMPROVING AFFINITY OF ANTIBODY FOR ANTIGEN AND USE THEREOF

CROSS REFERENCE TO RELATED APPLICATIONS

This application claims priority from prior Japanese Patent Application No. 2020-217336, filed on Dec. 25, 2020, entitled "Method for improving affinity of antibody for antigen and use thereof", the entire contents of which are incorporated herein by reference.

FIELD OF THE INVENTION

The present invention relates to a method for improving affinity of an antibody for an antigen. The present invention relates to a method for producing an antibody. The present invention relates to an antibody.

BACKGROUND

Conventionally, there has been known a technique for controlling affinity of an antibody for an antigen by modifying an amino acid sequence of a framework region (FR) of the antibody while maintaining the amino acid sequence of a complementarity determining region (CDR). For example, Fukunaga A. and Tsumoto K., Improving the affinity of an antibody for its antigen via long-range electrostatic interactions, Protein Eng. Des. Sel. Vol. 26, no. 12, pp. 773-780, 2013 describes that amino acid residues at position 68, 74 and 76 of heavy chain FR3 of a single chain antibody (scFv) binding to a basic epitope of troponin I were changed to aspartic acid residues that are acidic amino acids. Fukunaga A. and Tsumoto K., Improving the affinity of an antibody for its antigen via long-range electrostatic interactions, Protein Eng. Des. Sel. Vol. 26, no. 12, pp. 773-780, 2013 intends that affinity to troponin I is improved by utilizing electrical attraction generated by introduction of a charged amino acid residue into FR3. U.S. Patent Application Publication No. 2018/0179298 describes control of affinity of an antibody for an antigen by changing at least 3 amino acid residues in FR3 of a light chain to charged amino acid residues. In U.S. Patent Application Publication No. 2018/0179298, an amino acid sequence of FR of an antibody is modified according to electrical characteristics based on an amino acid sequence of CDR of the antibody rather than surface charge of the antigen.

SUMMARY OF THE INVENTION

The scope of the present invention is defined solely by the appended claims, and is not affected to any degree by the statements within this summary.

The present invention provides a method for improving affinity of an antibody for an antigen, the method comprising: in the antibody, changing at least 3 amino acid residues of framework region 3 (FR3) as defined by Kabat method to arginine residues or lysine residues, thereby improving affinity of an antibody for an antigen as compared with that of an antibody before said at least 3 amino acid residues are changed to arginine residues or lysine residues, wherein said at least 3 amino acid residues comprise at least 3 selected from the group consisting of amino acid residues at positions 68, 70, 72, 74, 75, 77, 79, 81, 82A, 82B, 83, 84, 85 and 87 of a heavy chain as defined by the Kabat method.

The present invention provides a method for producing an antibody, the method comprising: generating an antibody in which at least 3 amino acid residues of framework region 3 (FR3) as defined by Kabat method are arginine residues or lysine residues; and recovering the antibody generated in the generating, wherein affinity of the recovered antibody for an antigen is higher than affinity of an antibody in which said at least 3 amino acid residues are amino acid residues other than arginine residues and lysine residues, and said at least 3 amino acid residues comprise at least 3 selected from the group consisting of amino acid residues at positions 68, 70, 72, 74, 75, 77, 79, 81, 82A, 82B, 83, 84, 85 and 87 of a heavy chain as defined by the Kabat method.

The present invention provides an antibody, wherein at least 3 amino acid residues of framework region 3 (FR3) as defined by Kabat method are arginine residues or lysine residues, said at least 3 amino acid residues comprise at least 3 selected from the group consisting of amino acid residues at positions 68, 70, 72, 74, 75, 77, 79, 81, 82A, 82B, 83, 84, 85 and 87 of a heavy chain as defined by the Kabat method, and affinity for an antigen is higher than affinity of an original antibody in which said at least 3 amino acid residues are amino acid residues other than arginine residues and lysine residues.

BRIEF DESCRIPTION OF THE DRAWINGS

FIG. 6A is a light chain of wild-type humanized anti-HER2 antibody (SEQ ID NO: 1).

FIG. 6B is a heavy chain of wild-type humanized anti-HER2 antibody (SEQ ID NO: 2).

FIG. 6C is a heavy chain of Fab fragment of wild-type humanized anti-HER2 antibody (SEQ ID NO: 3).

DETAILED DESCRIPTION OF THE PREFERRED EMBODIMENTS

Figure 1:
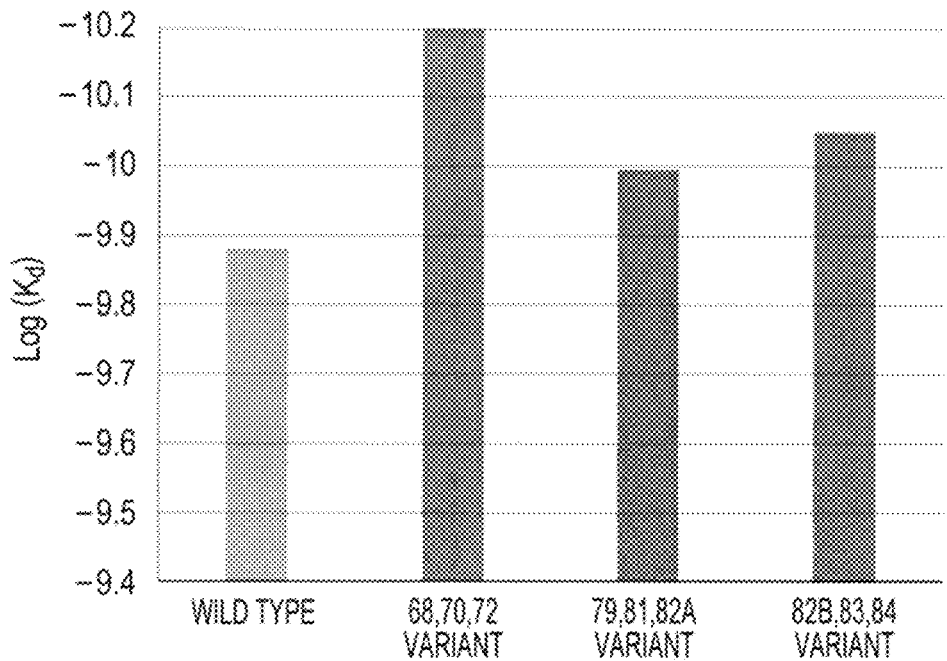
FIG. 1 is a graph showing affinity (logarithm of $K_d$ value) of a wild-type anti-lysozyme antibody and its variants for an antigen.

In the method for improving affinity of an antibody for an antigen of the present embodiment (hereinafter, also simply referred to as "method"), at least 3 amino acid residues among amino acid residues at positions 68, 70, 72, 74, 75, 77, 79, 81, 82A, 82B, 83, 84, 85 and 87 of a heavy chain as defined by the Kabat method in the amino acid sequence of the antibody are changed to arginine residues or lysine residues. Thereby, affinity of an antibody for an antigen is improved as compared with that of an antibody before the at least 3 amino acid residues are changed to arginine residues or lysine residues. The amino acid residues at positions 68, 70, 72, 74, 75, 77, 79, 81, 82A, 82B, 83, 84, 85 and 87 of the heavy chain as defined by the Kabat method are amino acid residues in heavy chain FR3 of the antibody. In the present specification, to "improve" affinity for an antigen has the same meaning as to "increase" affinity for an antigen.

FR is a region other than CDRs, present in each variable region of the light chain and heavy chain of the antibody. FR plays a role of a scaffold linking three CDRs and contributes to structural stability of the CDR. Therefore, the amino acid sequence of FR is highly conserved between antibodies of the same species. Each variable region of the light chain and heavy chain has three CDRs, CDR1, CDR2 and CDR3, and four FRs, FR1, FR2, FR3 and FR4. These are arranged in the order of FR1, CDR1, FR2, CDR2, FR3, CDR3 and FR4 from the N-terminal side of the variable region.

In the art, a method of numbering the amino acid residues of the CDR (hereinafter, also referred to as "numbering method") for defining the boundary and length of the CDR is known. When the amino acid residues of CDR are numbered by the numbering method, the amino acid residues of FR are also numbered. Examples of the numbering method include Kabat method (Kabat E A. et al., Sequences of Proteins of Immunological Interest., NIH publication No. 91-3242), Chothia method (Chothia C. and Lesk A M., Canonical Structures for the Hypervariable Regions of Immunoglobulins., J Mol Biol., vol. 196, pp. 901-917, 1987), IMGT method (Lefranc M P. et al., Developmental and Comparative Immunology, vol. 29, pp. 185-203, 2005), Honergger method (Honegger A. et al., Yet Another Numbering Scheme for Immunoglobulin Variable Domains: An Automatic Modeling and Analysis Tool., J Mol Biol., vol. 309, pp. 657-670, 2001), ABM method, Contact method, and the like.

In the present embodiment, the FR of an antibody may be defined by any numbering method, but is preferably defined by the Kabat method. According to the definition by the Kabat method, heavy chain FR3 of the antibody is defined as a region consisting of amino acid residues at positions 66 to 94 of the heavy chain.

In the method of the present embodiment, a first antibody in which at least 3 amino acid residues of heavy chain FR3 are changed to arginine residues or lysine residues is hereinafter also called "original antibody". In the present specification, the "original antibody" means an antibody having an amino acid sequence before applying the method of the present embodiment.

In the amino acid sequence of the original antibody, changing at least 3 predetermined amino acid residues to arginine residues or lysine residues is hereinafter also referred to as "modify" or "modification". An antibody obtained by the method for improving affinity of the present embodiment is hereinafter also called a "modified antibody" or a "variant".

In the present embodiment, the original antibody is not particularly limited. Since it is not necessary to change the amino acid sequence of CDR in the method of the present embodiment, the original antibody may be an antibody that recognizes any antigen. In a preferred embodiment, the original antibody is an antibody in which a base sequence of a gene encoding a variable region is known or an antibody in which the base sequence can be confirmed. Examples of such an antibody include an antibody in which a base sequence of an antibody gene is disclosed in a known database, an antibody from which an antibody-producing hybridoma is available, and the like. Examples of such a database include GeneBank, abYsis, IMGT, and the like.

The original antibody includes not only an antibody having a natural amino acid sequence (wild-type antibody) but also an antibody in which the amino acid sequence is artificially changed by a method other than the method for improving affinity of an antibody for an antigen of the present embodiment. Examples of the antibody in which the amino acid sequence has been artificially changed include an antibody in which an amino acid sequence of CDR has been changed, a chimeric antibody, a humanized antibody, a bispecific antibody, a single-chain antibody (scFv) in a chimeric antigen receptor, and the like.

The original antibody may be an antibody derived from any animal, and examples thereof include antibodies derived from mouse, rat, hamster, rabbit, goat, horse, chicken, human, and the like. Class of original antibody may be any of IgG, IgA, IgM, IgD and IgE, and is preferably IgG. The original antibody may be an antibody fragment as long as it has a variable region of a heavy chain. Examples of such an antibody fragment include Fab, Fab', F(ab')2, Fd, Fd', Fv, scFv, domain antibody (dAb), reduced IgG (rIgG), diabody, triabody, and the like. Among them, Fab is particularly preferable. In the present specification, the "antibody" is a concept including the "antibody fragment".

As an example of the original antibody, amino acid sequences of a light chain and a heavy chain of a humanized anti-HER2 antibody (trastuzumab) and an amino acid sequence of a heavy chain of Fab are shown in FIGS. 6A-6C, respectively. In FIGS. 6A-6C, the underlined parts indicate a variable region, and the gray marker parts indicate CDRs.

The amino acid sequences of each CDR and variable region of the light chain of the wild-type humanized anti-HER2 antibody are as follows.

```
Light chain CDR1:
                                          (SEQ ID NO: 4)
RASQDVNTAVA Light chain CDR2:
                                          (SEQ ID NO: 5)
SASFLYS Light chain CDR3:
                                          (SEQ ID NO: 6)
QQHYTTPPT Variable region:
                                          (SEQ ID NO: 7)
DIQMTQSPSSLSASVGDRVTITCRASQDVNTAVAWYQQKPGKAPKLLI

YSASFLYSGVPSRFSGSRSGTDFTLTISSLQPEDFATYYCQQHYTTPPTF

GQGTKVEIKRTV
```

The amino acid sequences of each CDR and variable region of the heavy chain of the wild-type humanized anti-HER2 antibody are as follows.

```
Heavy chain CDR1:
                                          (SEQ ID NO: 8)
DTYIH Heavy chain CDR2:
                                          (SEQ ID NO: 9)
RIYPTNGYTRYADSVKG Heavy chain CDR3:
                                          (SEQ ID NO: 10)
WGGDGFYAMDY
```

-continued

Variable region:
(SEQ ID NO: 11)
EVQLVESGGGLVQPGGSLRLSCAASGFNIKDTYIHWVRQAPGKGLEW

VARIYPTNGYTRYADSVKGRFTISADTSKNTAYLQMNSLRAEDTAVYYCS

RWGGDGFYAMDYWGQGTLVTVSS

Since the CDR is involved in specificity of the antibody, it is preferable that the amino acid sequence of CDR is not changed in the method of the present embodiment. That is, the amino acid sequence of the CDR of the modified antibody is preferably the same as the amino acid sequence of the CDR of the original antibody.

In the present embodiment, the affinity of the modified antibody for an antigen may be evaluated by a kinetic parameter in an antigen-antibody reaction or may be evaluated by an immunological measurement method such as an ELISA method. Examples of the kinetic parameter include dissociation constant ($K_d$), binding rate constant ($k_{on}$), and dissociation rate constant ($k_{off}$). Among them, $K_d$ is preferable. The kinetic parameter in an antigen-antibody reaction can be obtained by surface plasmon resonance (SPR) technology or the like. The value of $K_d$ in the antigen-antibody reaction of the modified antibody is, for example, about ½, about ⅓, about ¼, about ⅕, about 1/10, about 1/20, about 1/50, about 1/100 or about 1/1000, as compared with that of the original antibody.

In the original antibody, amino acid residues at positions 68, 70, 72, 74, 75, 77, 79, 81, 82A, 82B, 83, 84, 85 and 87 of the heavy chain as defined by the Kabat method have the following features (a), (b) and (c):
  (a) in an amino acid sequence of heavy chain FR3, being amino acid residues other than a vernier zone residue;
  (b) in an amino acid sequence of heavy chain FR3, being present at positions such that the sum of amino acid frequencies of serine (S), threonine (T), aspartic acid (D) and glutamic acid (E) is 15% or more; and
  (c) in an amino acid sequence of heavy chain FR3, being amino acid residues showing a ratio of solvent-exposed surface area of 10% or more.

The term "vernier zone residue" is an amino acid residue contributing to structural stability of the CDR among the amino acid residues contained in the FR. The term "position" refers to a position of an amino acid residue in an amino acid sequence. The position of each amino acid residue in the amino acid sequence of FR is indicated by a number assigned by numbering method.

The term "amino acid frequency" is also called amino acid appearance frequency, and refers to a ratio indicating how much predetermined amino acid appears at each position of a plurality of amino acid sequences when aligning these amino acid sequences. The amino acid frequency itself is a known index. Amino acid sequence alignment means aligning a plurality of amino acid sequences in a comparable manner. Amino acid sequence alignment can be performed by, for example, a known multiple alignment program such as ClustalW or TREBMAL. A method for calculating amino acid frequency itself is known, and amino acid frequency can be calculated by the above multiple alignment program or the like. Amino acid sequence alignment and amino acid frequency calculation can also be performed by abYsis of a public database that provides amino acid sequences of antibodies. For example, when an amino acid appears in all of a plurality of amino acid sequences at a predetermined position of the plurality of aligned amino acid sequences, amino acid frequency of the amino acid at that position is 100%. When an amino acid appears in half of a plurality of amino acid sequences at a predetermined position of the plurality of aligned amino acid sequences, amino acid frequency of the amino acid at that position is 50%. When an amino acid never appears at a predetermined position of a plurality of aligned amino acid sequences, amino acid frequency of the amino acid at that position is 0%.

When amino acid frequency in the amino acid sequence of the heavy chain of the antibody is calculated, amino acid sequences of heavy chains of a plurality of reference antibodies are obtained as a plurality of amino acid sequences. Then, the amino acid sequences of heavy chains of a plurality of reference antibodies are aligned so that numbers of the amino acid residues in FR assigned by a predetermined numbering method match among the amino acid sequences of heavy chains of a plurality of reference antibodies. The sum of amino acid frequencies of S, T, D and E in the amino acid sequence of heavy chain FR3 can be calculated as in Reference Example described later.

In the art, the term "solvent-exposed surface area" is defined as a locus surface of a center of a probe sphere (1.4 Å) when the probe sphere assuming a water molecule is rolled so as to be in contact with a surface (Van der Waals surface) of a protein molecule. The solvent-exposed surface area itself is a known index. The solvent-exposed surface area of a protein can be obtained from three-dimensional structure data of the protein by a known program or software such as SURFace, GETAREA, or Discovery Studio. It is also possible to obtain the solvent-exposed surface area of each amino acid residue in the protein. The solvent-exposed surface area of the amino acid residue in the protein differs depends on a size of side chain of the amino acid. Therefore, the term "ratio of solvent-exposed surface area" is used as an index standardizing the solvent-exposed surface area of the amino acid residue in the protein by the size of side chain of the amino acid. The ratio of solvent-exposed surface area itself is a known index. The ratio of solvent-exposed surface area in the amino acid sequence of heavy chain FR3 can be calculated as in Reference Example described later.

In the present embodiment, the number of amino acid residues modified in the heavy chain FR3 is, for example, 3, 4, 5, 6, 7, 8, 9, 10, 11, 12, 13 or 14.

In the modified antibody, amino acid residues after being modified from amino acid residues of the original antibody may be all arginine residues or all lysine residues. Alternatively, a part of the amino acid residues after being modified from the amino acid residues of the original antibody may be arginine residues, and the rest may be lysine residues.

In the present embodiment, amino acid residues at positions 68, 70, 72, 74, 75, 77, 79, 81, 82A, 82B, 83, 84, 85 and 87 of the heavy chain as defined by the Kabat method in the original antibody are preferably other than arginine residues and lysine residues. The amino acid residue in the original antibody may be, for example, a neutral amino acid residue, an acidic amino acid residue, or a histidine residue. The neutral amino acid residue refers to an alanine residue, an asparagine residue, an isoleucine residue, a glycine residue, a glutamine residue, a cysteine residue, a threonine residue, a serine residue, a tyrosine residue, a phenylalanine residue, a proline residue, a valine residue, a methionine residue, a leucine residue, and a tryptophan residue. The acidic amino acid residue is an aspartic acid residue and a glutamic acid residue.

Examples of means for modifying an amino acid residue include substitution and insertion of an amino acid residue, and the like. In modification by substitution of amino acid residues, at least 3 amino acid residues selected from positions 68, 70, 72, 74, 75, 77, 79, 81, 82A, 82B, 83, 84, 85 and 87 of the heavy chain as defined by the Kabat method are substituted from amino acid residues other than arginine residues and lysine residues to arginine residues or lysine residues. Thereby, the at least 3 amino acid residues change to arginine residues or lysine residues.

In modification by insertion of amino acid residues, at least 3 arginine residues or lysine residues are inserted in the amino acid sequence of the original antibody so that the arginine residues or lysine residues are located in at least 3 positions selected from positions 68, 70, 72, 74, 75, 77, 79, 81, 82A, 82B, 83, 84, 85 and 87 of the heavy chain as defined by the Kabat method. For example, when it is desired to change amino acid residues at positions 68, 70 and 72 of the heavy chain as defined by the Kabat method to arginine residues, arginine residues are inserted between an amino acid residue at position 67 and an amino acid residue at position 68, between the amino acid residue at position 68 and an amino acid residue at position 69, and between the amino acid residue at position 69 and an amino acid residue at position 70 of the heavy chain of the original antibody, respectively. Thereby, the 3 inserted arginine residues are respectively located at positions 68, 70 and 72 in the modified antibody.

In the original antibody, when any of the amino acid residues at positions 68, 70, 72, 74, 75, 77, 79, 81, 82A, 82B, 83, 84, 85 and 87 of the heavy chain as defined by the Kabat method is an arginine residue or a lysine residue, the amino acid residue may be left as it is. In this case, among the amino acid residues at positions 68, 70, 72, 74, 75, 77, 79, 81, 82A, 82B, 83, 84, 85 and 87 of the heavy chain, at least 3 may be selected from amino acid residues other than arginine residues and lysine residues.

In one embodiment, the at least 3 amino acid residues changed to arginine residues or lysine residues in the heavy chain FR3 may include at least 1 selected from amino acid residues at positions 75, 77, 79, 81, 82A, 82B, 83, 84, 85 and 87 of the heavy chain as defined by the Kabat method. For example, the at least 3 amino acid residues may include at least 2 selected from amino acid residues at positions 68, 70, 72 and 74 of the heavy chain as defined by the Kabat method and at least 1 selected from the amino acid residues at positions 75, 77, 79, 81, 82A, 82B, 83, 84, 85 and 87 of the heavy chain as defined by the Kabat method. Alternatively, the at least 3 amino acid residues may include at least 1 selected from the amino acid residues at positions 68, 70, 72 and 74 of the heavy chain as defined by the Kabat method and at least 2 selected from the amino acid residues at positions 75, 77, 79, 81, 82A, 82B, 83, 84, 85 and 87 of the heavy chain as defined by the Kabat method. Alternatively, the at least 3 amino acid residues may include at least 3 selected from the amino acid residues at positions 75, 77, 79, 81, 82A, 82B, 83, 84, 85 and 87 of the heavy chain as defined by the Kabat method.

In one embodiment, the at least 3 amino acid residues changed to arginine residues or lysine residues in the heavy chain FR3 may include the amino acid residue at position 72 of the heavy chain as defined by the Kabat method. For example, the at least 3 amino acid residues may include at least 2 selected from the amino acid residue at position 72 of the heavy chain as defined by the Kabat method and the amino acid residues at positions 68, 70, 74, 75, 77, 79, 81, 82A, 82B, 83, 84, 85 and 87 of the heavy chain as defined by the Kabat method. Alternatively, the at least 3 amino acid residues may include at least 2 selected from the amino acid residue at position 72 of the heavy chain as defined by the Kabat method and the amino acid residues at positions 75, 77, 79, 81, 82A, 82B, 83, 84, 85 and 87 of the heavy chain as defined by the Kabat method.

In one embodiment, at least 3 amino acid residues changed to arginine residues or lysine residues in the heavy chain FR3 may be, for example, any of the following 1) to 6):
1) Amino acid residues at positions 68, 70 and 72 of the heavy chain as defined by the Kabat method;
2) Amino acid residues at positions 72, 77 and 79 of the heavy chain as defined by the Kabat method;
3) Amino acid residues at positions 74, 75 and 77 of the heavy chain as defined by the Kabat method;
4) Amino acid residues at positions 79, 81 and 82A of the heavy chain as defined by the Kabat method;
5) Amino acid residues at positions 82B, 83 and 84 of the heavy chain as defined by the Kabat method; and
6) Amino acid residues at positions 84, 85 and 87 of the heavy chain as defined by the Kabat method.

In a further embodiment, in the original antibody, at least 3 amino acid residues of the heavy chain FR3 as defined by the Kabat method may be changed to arginine residues or lysine residues, and at least 3 amino acid residues of light chain FR as defined by the Kabat method may be changed to arginine residues or lysine residues. Thereby, the affinity for an antigen can be improved not only as compared with that of the original antibody, but also as compared with that of an antibody in which only the heavy chain FR3 is modified. Such amino acid residues of the light chain FR include at least 3 selected from amino acid residues at positions 1, 3, 5, 7, 9, 10, 12, 14, 17, 18, 20, 22, 60, 63, 65, 67, 69, 70, 72, 74, 76, 77, 79 and 81 of the light chain as defined by the Kabat method. Modification of the light chain FR can be performed in the same manner as the modification of the heavy chain FR3.

According to the definition by the Kabat method, FR1 of the light chain is defined as a region consisting of amino acid residues at positions 1 to 23 of the light chain, and FR3 of the light chain is defined as a region consisting of amino acid residues at positions 57 to 88 of the light chain. That is, the amino acid residues at positions 1, 3, 5, 7, 9, 10, 12, 14, 17, 18, 20 and 22 of the light chain as defined by the Kabat method are present in the light chain FR1, and the amino acid residues at positions 60, 63, 65, 67, 69, 70, 72, 74, 76, 77, 79 and 81 of the light chain as defined by the Kabat method are present in the light chain FR3.

In the present embodiment, the number of amino acid residues modified in the light chain FR is, for example, 3, 4, 5, 6, 7, 8, 9, 10, 11, 12, 13, 14, 15, 16, 17, 18, 19, 20, 21, 22, 23 or 24. When at least 3 amino acid residues are modified in the light chain FR1, the number of modified amino acid residues is, for example, 3, 4, 5, 6, 7, 8, 9, 10, 11 or 12. When at least 3 amino acid residues are modified in the light chain FR3, the number of modified amino acid residues is, for example, 3, 4, 5, 6, 7, 8, 9, 10, 11 or 12.

In one embodiment, in the original antibody, at least 3 amino acid residues of the heavy chain FR3 as defined by the Kabat method are changed to arginine residues or lysine residues, and at least 3 amino acid residues of the light chain FR3 as defined by the Kabat method are changed to arginine residues or lysine residues. In this case, the at least 3 amino acid residues of the light chain FR3 include at least 3 selected from the amino acid residues at positions 60, 63, 65, 67, 69, 70, 72, 74, 76, 77, 79 and 81 of the light chain as defined by the Kabat method. Preferably, the at least 3 amino acid residues changed to arginine residues or lysine residues in the light chain FR3 include the amino acid residues at positions 63, 65 and 67 of the light chain as defined by the Kabat method.

In one embodiment, the method for improving affinity of an antibody for an antigen includes, in the antibody, changing at least 3 amino acid residues of heavy chain FR3 as defined by Kabat method to arginine residues or lysine residues, and at least 3 amino acid residues of light chain FR as defined by Kabat method to arginine residues or lysine residues, thereby improving affinity of an antibody for an antigen as compared with that of an antibody before the at least 3 amino acid residues in each of the heavy chain FR3 and the light chain FR are changed to arginine residues or lysine residues, in which the at least 3 amino acid residues of the heavy chain FR3 include at least 3 selected from the amino acid residues at positions 68, 70, 72, 74, 75, 77, 79, 81, 82A, 82B, 83, 84, 85 and 87 of the heavy chain as defined by the Kabat method, and the at least 3 amino acid residues of the light chain FR include at least 3 selected from the amino acid residues at positions 1, 3, 5, 7, 9, 10, 12, 14, 17, 18, 20, 22, 60, 63, 65, 67, 69, 70, 72, 74, 76, 77, 79 and 81 of the light chain as defined by the Kabat method.

In one embodiment, the method for improving affinity of an antibody for an antigen includes, in the antibody, changing at least 3 amino acid residues of heavy chain FR3 as defined by Kabat method to arginine residues or lysine residues, and at least 3 amino acid residues of light chain FR3 as defined by Kabat method to arginine residues or lysine residues, thereby improving affinity of an antibody for an antigen as compared with that of an antibody before the at least 3 amino acid residues in each of the heavy chain FR3 and the light chain FR3 are changed to arginine residues or lysine residues, in which the at least 3 amino acid residues of the heavy chain FR3 include at least 3 selected from the amino acid residues at positions 68, 70, 72, 74, 75, 77, 79, 81, 82A, 82B, 83, 84, 85 and 87 of the heavy chain as defined by the Kabat method, and the at least 3 amino acid residues of the light chain FR3 include at least 3 selected from the amino acid residues at positions 60, 63, 65, 67, 69, 70, 72, 74, 76, 77, 79 and 81 of the light chain as defined by the Kabat method.

In one embodiment, at least 3 amino acid residues changed to arginine residues or lysine residues in each of the heavy chain FR3 and the light chain FR3 may be, for example, any of the following 7) to 12):

7) Amino acid residues at positions 68, 70 and 72 of the heavy chain as defined by the Kabat method and amino acid residues at positions 63, 65 and 67 of the light chain as defined by the Kabat method;
8) Amino acid residues at positions 72, 77 and 79 of the heavy chain as defined by the Kabat method and amino acid residues at positions 63, 65 and 67 of the light chain as defined by the Kabat method;
9) Amino acid residues at positions 74, 75 and 77 of the heavy chain as defined by the Kabat method and amino acid residues at positions 63, 65 and 67 of the light chain as defined by the Kabat method;
10) Amino acid residues at positions 79, 81 and 82A of the heavy chain as defined by the Kabat method and amino acid residues at positions 63, 65 and 67 of the light chain as defined by the Kabat method;
11) Amino acid residues at positions 82B, 83 and 84 of the heavy chain as defined by the Kabat method and amino acid residues at positions 63, 65 and 67 of the light chain as defined by the Kabat method; and
12) Amino acid residues at positions 84, 85 and 87 of the heavy chain as defined by the Kabat method and amino acid residues at positions 63, 65 and 67 of the light chain as defined by the Kabat method.

In the present embodiment, when an electrical characteristic of CDR based on an amino acid sequence of the CDR of the original antibody is neutral or negatively charged, at least 3 amino acid residues of the heavy chain FR3 or at least 3 amino acid residues of each of the heavy chain FR3 and the light chain FR may be changed to arginine residues or lysine residues. The "electrical characteristic of CDR" is an index uniquely defined by the present inventors. The electrical characteristic of CDR is determined based on the number of basic amino acid residues and acidic amino acid residues in the amino acid sequence of the CDR. The basic amino acid residue is a lysine residue, an arginine residue, and a histidine residue. Specifically, the electrical characteristic of CDR is determined by following formula (I).

$$Z = [\text{Number of basic amino acid residues in amino acid sequence of CDR}] - [\text{Number of acidic amino acid residues in amino acid sequence of CDR}] \quad (I)$$

wherein when Z is −1, 0 or 1, the electrical characteristic of CDR is neutral,
when Z is 2 or more, the electrical characteristic of CDR is positively charged, and
when Z is −2 or less, the electrical characteristic of CDR is negatively charged.

The electrical characteristic of CDR may be determined based on the amino acid sequence of CDR of a light chain and/or a heavy chain. When determining the electrical characteristic of CDR of the light chain, the amino acid sequence of the CDR in the formula (I) refers to all amino acid sequences of CDR1, CDR2 and CDR3 of the light chain. When determining the electrical characteristic of CDR of the heavy chain, the amino acid sequence of the CDR in the formula (I) refers to all amino acid sequences of CDR1, CDR2 and CDR3 of the heavy chain. Preferably, it is determined based on the amino acid sequences of the CDRs of both the light chain and heavy chain. In this case, the amino acid sequence of the CDR in the formula (I) refers to all amino acid sequences of CDR1, CDR2 and CDR3 of the light chain and CDR1, CDR2 and CDR3 of the heavy chain. In the present embodiment, in the original antibody whose electrical characteristic determined based on the amino acid sequences of CDRs of both the light chain and the heavy chain is neutral or negatively charged, the at least 3 amino acid residues may be changed to arginine residues or lysine residues.

The amino acid sequence of the CDR can be obtained from a public database that discloses the sequence of the antibody gene. Alternatively, when there is a hybridoma that produces an original antibody, the amino acid sequence of the CDR can be obtained by obtaining a nucleic acid encoding a heavy chain and a light chain from the hybridoma by a known method, and sequencing the base sequence of the nucleic acid.

The electrical characteristic of CDR differs depending on the antibody. For example, when CDRs are defined by the Kabat method, the electrical characteristic of CDR of a wild-type anti-lysozyme antibody (HyHEL-10) used in Examples described later is negatively charged (X=−3). The electrical characteristic of CDR of a wild-type humanized anti-HER2 antibody (trastuzumab) is neutral (X=0). In the method of the present embodiment, since the amino acid sequence of the CDR of the original antibody is not changed, the electrical characteristic of CDR of a modified antibody is the same as that of the original antibody.

In the method of the present embodiment, since at least 3 amino acid residues of heavy chain FR3 of the antibody are changed to arginine residues or lysine residues which are basic amino acid residues, it is considered that a positive charge is imparted to an antigen binding site of the modified antibody. On the other hand, it is considered that a mechanism by which affinity of the modified antibody for an antigen is improved as compared with that of the original antibody is not substantially related to an electrostatic interaction between the antigen binding site of the antibody and the antigen. For example, lysozyme is known to be a protein having an isoelectric point (PI) of about 10. That is, lysozyme is a positively charged antigen. Then, when the method of the present embodiment is applied to the wild-type anti-lysozyme antibody to modify the heavy chain FR3, the number of basic amino acid residues increases in a variable region. Therefore, it is considered that the affinity of the modified antibody for lysozyme rather decreases. However, as shown in Examples described later, all variants of the anti-lysozyme antibody have improved affinity for lysozyme. Thus, it is considered that the improvement of affinity of an antibody for an antigen by the method of the present embodiment does not depend on the charge of the antigen.

In the present embodiment, the amino acid residue of the original antibody can be changed to an arginine residue or a lysine residue by using known methods such as DNA recombination technology and other molecular biological techniques. Specifically, first, a polynucleotide encoding an amino acid sequence of the original antibody is obtained, and from this polynucleotide, a polynucleotide encoding an amino acid sequence of a modified antibody is prepared. Then, a modified antibody is generated by a protein expression system using the prepared polynucleotide. The protein expression system may be an expression system using a host cell or a cell-free protein synthesis system. Examples of the host cell include mammalian cells, insect cells, *E. coli*, yeast, and the like. Examples of the cell-free protein synthesis system include a wheat germ-derived synthesis system, an *E. coli*-derived synthesis system, a reconfiguration type cell-free protein synthesis system, and the like.

For example, when there is a hybridoma that produces the original antibody, a modified antibody can be obtained as follows. First, RNA extracted from the hybridoma is used to synthesize a polynucleotide encoding the heavy chain and a polynucleotide encoding the light chain of the original antibody, by a reverse transcription reaction and a RACE (rapid amplification of cDNA ends) method. Next, the polynucleotide encoding the heavy chain as a template is amplified by PCR using a primer for modifying at least 3 amino acid residues of heavy chain FR3 to obtain a polynucleotide encoding the heavy chain in which FR3 has been modified. The obtained polynucleotide and the polynucleotide encoding the light chain of the original antibody are incorporated into a known expression vector to obtain an expression vector containing a polynucleotide encoding a modified antibody. By transforming or transfecting the obtained expression vector into an appropriate host cell, an antibody with improved affinity is generated. A modified antibody can be obtained by recovering the generated modified antibody from the host cell. When the light chain FR is also modified, the obtained polynucleotide may be amplified by PCR using a primer for modifying at least 3 amino acid residues of the light chain FR to obtain a polynucleotide encoding the light chain in which FR has been modified.

In the present embodiment, the polynucleotide encoding the heavy chain and the polynucleotide encoding the light chain may be incorporated into one expression vector or may be separately incorporated into two expression vectors. The type of expression vector is not particularly limited, and can be determined according to the host cell. Examples thereof include expression vectors for mammalian cells, expression vectors for insect cells, expression vectors for *E. coli*, expression vectors for yeast, and the like.

When a modified antibody is obtained by a cell-free protein synthesis system, a polynucleotide encoding the heavy chain in which FR3 has been modified and a polynucleotide encoding the light chain of the original antibody are added to the cell-free protein synthesis system and incubated under appropriate conditions, thereby a modified antibody can be obtained. When the light chain FR is also modified, a polynucleotide encoding the light chain in which FR has been modified may be added instead of the polynucleotide encoding the light chain of the original antibody.

When obtaining a modified antibody which is a single chain antibody (scFv), as shown in, for example, PCT International Application Publication No. 2013/084371 A1, RNA extracted from the hybridoma that produces the original antibody may be used to synthesize a polynucleotide encoding a heavy chain variable region and a polynucleotide encoding a light chain variable region by a reverse transcription reaction and PCR. These polynucleotides are ligated by overlap extension PCR or the like to obtain a polynucleotide encoding the original antibody which is scFv. The obtained polynucleotide is amplified by PCR using a primer for modifying at least 3 amino acid residues of FR3 of the heavy chain variable region to obtain a polynucleotide encoding scFv in which FR3 of the heavy chain variable region has been modified. The obtained polynucleotide is incorporated into a known expression vector to obtain an expression vector containing a polynucleotide encoding a modified antibody which is scFv. By transforming or transfecting the obtained expression vector into an appropriate host cell, a modified antibody which is scFv can be obtained. When the light chain FR is also modified, the obtained polynucleotide may be amplified by PCR using a primer for modifying at least 3 amino acid residues of the light chain FR and a primer for modifying at least 3 amino acid residues of FR3 of the heavy chain variable region to obtain a polynucleotide encoding scFv in which FR3 of the heavy chain variable region and FR of the light chain variable region have been modified.

When there is no hybridoma that produces the original antibody, an antibody-producing hybridoma may be prepared by known methods such as those described in, for example, Kohler and Milstein, Nature, vol.256, pp.495-497, 1975. Alternatively, RNA obtained from the spleen of an animal such as a mouse immunized with an antigen of interest may be used. When using the RNA obtained from the spleen, for example, as shown in Fukunaga A and Tsumoto K, Protein Eng. Des. Sel. 2013, vol.26, pp.773-780, a polynucleotide encoding scFv having a desired affinity as an original antibody may be selected by a phage display method or the like, from the obtained polynucleotides encoding scFv.

A method of recovering an antibody generated by a protein expression system is known per se. For example, when an antibody is generated in a host cell, the host cell may be dissolved in a solution containing an appropriate solubilizer to liberate the antibody in the solution. When the host cell secretes the generated antibody from the inside of the cell into a medium, a culture supernatant may be recovered. In a cell-free protein synthesis system, the synthesized antibody is contained in a reaction solution. The antibody liberated in a liquid can be recovered by a known method such as affinity chromatography. For example, when the generated antibody is IgG, the antibody can be recovered by affinity chromatography using protein A or G. If necessary, the recovered antibody may be purified by a known method such as gel filtration.

The modified antibody of the present embodiment can be used, for example, as an active ingredient for various tests and studies, diagnostic agents, or therapeutic agents. The modified antibody may be modified with a known substance such as a fluorescent dye, an enzyme, a radioisotope, biotin, or an anticancer agent.

The antibody of the present embodiment is an antibody in which at least 3 selected from the amino acid residues at positions 68, 70, 72, 74, 75, 77, 79, 81, 82A, 82B, 83, 84, 85 and 87 of the heavy chain as defined by the Kabat method are arginine residues or lysine residues. The antibody of the present embodiment is characterized in that the affinity for an antigen is higher than that of an antibody in which the at least 3 amino acid residues are amino acid residues other than arginine residues and lysine residues. The antibody whose affinity is to be compared can be an antibody that recognizes the same antigen as the antibody of the present embodiment.

A means for evaluating affinity of an antibody for an antigen of the present embodiment is the same as described for the method of the present embodiment described above. The value of $K_d$ in the antigen-antibody reaction of the antibody of the present embodiment is, for example, about ½, about ⅓, about ¼, about ⅕, about 1/10, about 1/20, about 1/50, about 1/100 or about 1/1000, as compared with an antibody in which the at least 3 amino acid residues are amino acid residues other than arginine residues and lysine residues.

The antibody of the present embodiment may be an antibody that recognizes any antigen, or may be a bispecific antibody. The antibody of the present embodiment may be an antibody derived from any animal such as mouse, rat, hamster, rabbit, goat, horse, chicken, and human, and may be a chimeric antibody or a humanized antibody. Class of antibody of the present embodiment may be any of IgG, IgA, IgM, IgD and IgE, and is preferably IgG. The antibody of the present embodiment may be an antibody fragment as long as it has a variable region of a heavy chain. Examples of such an antibody fragment include Fab, Fab', F(ab')2, Fd, Fd', Fv, scFv, dAb, rIgG, diabody, triabody, and the like. Among them, Fab is particularly preferable.

In the antibody of the present embodiment, among the amino acid residues at positions 68, 70, 72, 74, 75, 77, 79, 81, 82A, 82B, 83, 84, 85 and 87 of the heavy chain as defined by the Kabat method, the number of arginine residues or lysine residues is, for example, 3, 4, 5, 6, 7, 8, 9, 10, 11, 12, 13 or 14.

In the antibody of the present embodiment, the at least 3 amino acid residues may be those changed from amino acid residues other than arginine residues and lysine residues to arginine residues or lysine residues by substitution or insertion of amino acid residues. In a preferred embodiment, the at least 3 amino acid residues may be those substituted from amino acid residues other than arginine residues and lysine residues to arginine residues or lysine residues.

In one embodiment, the at least 3 amino acid residues that are arginine residues or lysine residues in the heavy chain FR3 may include at least 1 selected from the amino acid residues at positions 75, 77, 79, 81, 82A, 82B, 83, 84, 85 and 87 of the heavy chain as defined by the Kabat method. For example, the at least 3 amino acid residues may include at least 2 selected from amino acid residues at positions 68, 70, 72 and 74 of the heavy chain as defined by the Kabat method and at least 1 selected from the amino acid residues at positions 75, 77, 79, 81, 82A, 82B, 83, 84, 85 and 87 of the heavy chain as defined by the Kabat method. Alternatively, the at least 3 amino acid residues may include at least 1 selected from the amino acid residues at positions 68, 70, 72 and 74 of the heavy chain as defined by the Kabat method and at least 2 selected from the amino acid residues at positions 75, 77, 79, 81, 82A, 82B, 83, 84, 85 and 87 of the heavy chain as defined by the Kabat method. Alternatively, the at least 3 amino acid residues may include at least 3 selected from the amino acid residues at positions 75, 77, 79, 81, 82A, 82B, 83, 84, 85 and 87 of the heavy chain as defined by the Kabat method.

In one embodiment, the at least 3 amino acid residues that are arginine residues or lysine residues in the heavy chain FR3 may include the amino acid residue at position 72 of the heavy chain as defined by the Kabat method. For example, the at least 3 amino acid residues may include at least 2 selected from the amino acid residue at position 72 of the heavy chain as defined by the Kabat method and the amino acid residues at positions 68, 70, 74, 75, 77, 79, 81, 82A, 82B, 83, 84, 85 and 87 of the heavy chain as defined by the Kabat method. Alternatively, the at least 3 amino acid residues may include at least 2 selected from the amino acid residue at position 72 of the heavy chain as defined by the Kabat method and the amino acid residues at positions 75, 77, 79, 81, 82A, 82B, 83, 84, 85 and 87 of the heavy chain as defined by the Kabat method.

In one embodiment, at least 3 amino acid residues that are arginine residues or lysine residues in the heavy chain FR3 may be, for example, any of 1) to 6) described above.

In the antibody of the present embodiment, at least 3 amino acid residues of the heavy chain FR3 as defined by the Kabat method may be arginine residues or lysine residues, and at least 3 amino acid residues of the light chain FR as defined by the Kabat method may be arginine residues or lysine residues. Such amino acid residues of the light chain FR include at least 3 selected from the amino acid residues at positions 1, 3, 5, 7, 9, 10, 12, 14, 17, 18, 20, 22, 60, 63, 65, 67, 69, 70, 72, 74, 76, 77, 79 and 81 of the light chain as defined by the Kabat method. The antibody of the present embodiment in which at least 3 amino acid residues of each of the heavy chain FR3 and the light chain FR are arginine residues or lysine residues has improved affinity for an antigen as compared with that of the antibody of the present embodiment in which at least 3 amino acid residues of the heavy chain FR3 are arginine residues or lysine residues.

When at least 3 amino acid residues of the light chain FR of the antibody of the present embodiment are arginine residues or lysine residues, the number of arginine residues or lysine residues among the amino acid residues at positions 1, 3, 5, 7, 9, 10, 12, 14, 17, 18, 20, 22, 60, 63, 65, 67, 69, 70, 72, 74, 76, 77, 79 and 81 of the light chain as defined by the Kabat method is, for example, 3, 4, 5, 6, 7, 8, 9, 10, 11, 12, 13, 14, 15, 16, 17, 18, 19, 20, 21, 22, 23 or 24. When at least 3 amino acid residues of the light chain FR1 are arginine residues or lysine residues, the number of arginine residues or lysine residues among the amino acid residues at positions 1, 3, 5, 7, 9, 10, 12, 14, 17, 18, 20 and 22 of the light chain as defined by the Kabat method is, for example, 3, 4, 5, 6, 7, 8, 9, 10, 11 or 12. When at least 3 amino acid residues of the light chain FR3 are arginine residues or lysine residues, the number of arginine residues or lysine residues among the amino acid residues at positions 60, 63, 65, 67, 69, 70, 72, 74, 76, 77, 79 and 81 of the light chain as defined by the Kabat method is, for example, 3, 4, 5, 6, 7, 8, 9, 10, 11 or 12.

The antibody of the present embodiment can be an antibody in which at least 3 amino acid residues of the heavy chain FR3 as defined by the Kabat method are arginine residues or lysine residues, and at least 3 amino acid residues of the light chain FR3 as defined by the Kabat method are arginine residues or lysine residues. In this case, the at least 3 amino acid residues of the light chain FR3 include at least 3 selected from the amino acid residues at positions 60, 63, 65, 67, 69, 70, 72, 74, 76, 77, 79 and 81 of the light chain as defined by the Kabat method. Preferably, at least 3 amino acid residues of the light chain FR3 include the amino acid residues at positions 63, 65 and 67 of the light chain as defined by the Kabat method.

The antibody of the present embodiment can be an antibody in which at least 3 amino acid residues of the heavy chain FR3 as defined by the Kabat method are arginine residues or lysine residues, at least 3 amino acid residues of the light chain FR as defined by the Kabat method are arginine residues or lysine residues, at least 3 amino acid residues of the heavy chain FR3 include at least 3 selected from the amino acid residues at positions 68, 70, 72, 74, 75, 77, 79, 81, 82A, 82B, 83, 84, 85 and 87 of the heavy chain as defined by the Kabat method, and the at least 3 amino acid residues of the light chain FR include at least 3 selected from the amino acid residues at positions 1, 3, 5, 7, 9, 10, 12, 14, 17, 18, 20, 22, 60, 63, 65, 67, 69, 70, 72, 74, 76, 77, 79 and 81 of the heavy chain as defined by the Kabat method, and the affinity for an antigen is higher than that of an antibody in which at least 3 amino acid residues of each of the heavy chain FR3 and the light chain FR are amino acid residues other than arginine residues and lysine residues.

The antibody of the present embodiment can be an antibody in which at least 3 amino acid residues of the heavy chain FR3 as defined by the Kabat method are arginine residues or lysine residues, at least 3 amino acid residues of the light chain FR3 as defined by the Kabat method are arginine residues or lysine residues, at least 3 amino acid residues of the heavy chain FR3 include at least 3 selected from the amino acid residues at positions 68, 70, 72, 74, 75, 77, 79, 81, 82A, 82B, 83, 84, 85 and 87 of the heavy chain as defined by the Kabat method, and at least 3 amino acid residues of the light chain FR include at least 3 selected from the amino acid residues at positions 60, 63, 65, 67, 69, 70, 72, 74, 76, 77, 79 and 81 of the heavy chain as defined by the Kabat method, and the affinity for an antigen is higher than that of an antibody in which at least 3 amino acid residues of each of the heavy chain FR3 and the light chain FR3 are amino acid residues other than arginine residues and lysine residues.

In one embodiment, at least 3 amino acid residues that are arginine residues or lysine residues in each of the heavy chain FR3 and the light chain FR3 may be, for example, any of 7) to 12) described above.

In the antibody of the present embodiment, the electrical characteristic of CDR based on the amino acid sequence of the CDR can be neutral or negatively charged. The electrical characteristic of CDR is determined by the above formula (I).

The antibody of the present embodiment can be obtained by the method for producing an antibody of the present embodiment (hereinafter, also referred to as "production method"). In the production method of the present embodiment, first, an antibody is generated in which at least 3 amino acid residues selected from the amino acid residues at positions 68, 70, 72, 74, 75, 77, 79, 81, 82A, 82B, 83, 84, 85 and 87 of the heavy chain as defined by the Kabat method are arginine residues or lysine residues. The antibody can be generated, for example, by substitution or insertion of an amino acid residue in any antibody. Any antibody is preferably an antibody in which the at least 3 amino acid residues are other than arginine residues and lysine residues.

Generation of an antibody by substitution of amino acid residues includes, in any antibody, substituting at least 3 amino acid residues selected from positions 68, 70, 72, 74, 75, 77, 79, 81, 82A, 82B, 83, 84, 85 and 87 of the heavy chain as defined by the Kabat method from amino acid residues other than arginine residues and lysine residues to arginine residues or lysine residues. Generation of an antibody by insertion of amino acid residues includes inserting at least 3 arginine residues or lysine residues in the amino acid sequence of any antibody so that the arginine residues or lysine residues are located in at least 3 positions selected from positions 68, 70, 72, 74, 75, 77, 79, 81, 82A, 82B, 83, 84, 85 and 87 of the heavy chain as defined by the Kabat method.

In the present embodiment, in any antibody described above, the electrical characteristic of CDR based on the amino acid sequence of the CDR can be neutral or negatively charged. The electrical characteristic of CDR is determined by the above formula (I).

In one embodiment, the at least 3 amino acid residues that are arginine residues or lysine residues in the heavy chain FR3 of the generated antibody may include at least 1 selected from the amino acid residues at positions 75, 77, 79, 81, 82A, 82B, 83, 84, 85 and 87 of the heavy chain as defined by the Kabat method. Such at least 3 amino acid residues may include, for example, at least 2 selected from the amino acid residues at positions 68, 70, 72 and 74 of the heavy chain as defined by the Kabat method and at least 1 selected from the amino acid residues at positions 75, 77, 79, 81, 82A, 82B, 83, 84, 85 and 87 of the heavy chain as defined by the Kabat method. Alternatively, the at least 3 amino acid residues may include at least 1 selected from the amino acid residues at positions 68, 70, 72 and 74 of the heavy chain as defined by the Kabat method and at least 2 selected from the amino acid residues at positions 75, 77, 79, 81, 82A, 82B, 83, 84, 85 and 87 of the heavy chain as defined by the Kabat method. Alternatively, the at least 3 amino acid residues may include at least 3 selected from the amino acid residues at positions 75, 77, 79, 81, 82A, 82B, 83, 84, 85 and 87 of the heavy chain as defined by the Kabat method.

In one embodiment, the at least 3 amino acid residues that are arginine residues or lysine residues in the heavy chain FR3 of the generated antibody may include the amino acid residue at position 72 of the heavy chain as defined by the Kabat method. Such at least 3 amino acid residues may include, for example, at least 2 selected from the amino acid residue at position 72 of the heavy chain as defined by the Kabat method and the amino acid residues at positions 68, 70, 74, 75, 77, 79, 81, 82A, 82B, 83, 84, 85 and 87 of the heavy chain as defined by the Kabat method. Alternatively, the at least 3 amino acid residues may include at least 2 selected from the amino acid residue at position 72 of the heavy chain as defined by the Kabat method and the amino acid residues at positions 75, 77, 79, 81, 82A, 82B, 83, 84, 85 and 87 of the heavy chain as defined by the Kabat method.

In one embodiment, at least 3 amino acid residues that are arginine residues or lysine residues in the heavy chain FR3 of the generated antibody may be, for example, any of 1) to 6) described above.

In the production method of the present embodiment, in the generated antibody, at least 3 amino acid residues of the heavy chain FR3 as defined by the Kabat method may be arginine residues or lysine residues, and at least 3 amino acid residues of the light chain FR as defined by the Kabat method may be arginine residues or lysine residues. Such amino acid residues of the light chain FR include at least 3 selected from the amino acid residues at positions 1, 3, 5, 7, 9, 10, 12, 14, 17, 18, 20, 22, 60, 63, 65, 67, 69, 70, 72, 74, 76, 77, 79 and 81 of the light chain as defined by the Kabat method.

In the production method of the present embodiment, the generated antibody can be an antibody in which at least 3 amino acid residues of the heavy chain FR3 as defined by the Kabat method are arginine residues or lysine residues, and at least 3 amino acid residues of the light chain FR3 as defined by the Kabat method are arginine residues or lysine residues. In this case, the at least 3 amino acid residues of the light chain FR3 include at least 3 selected from the amino acid residues at positions 60, 63, 65, 67, 69, 70, 72, 74, 76, 77, 79 and 81 of the light chain as defined by the Kabat method. Preferably, at least 3 amino acid residues of the light chain FR3 include the amino acid residues at positions 63, 65 and 67 of the light chain as defined by the Kabat method.

In one embodiment, the method for producing an antibody includes: generating an antibody in which at least 3 amino acid residues of the heavy chain FR3 as defined by the Kabat method are arginine residues or lysine residues and at least 3 amino acid residues of the light chain FR as defined by the Kabat method are arginine residues or lysine residues; and recovering the antibody generated in the generating, in which affinity of the recovered antibody for an antigen is higher than affinity of an antibody in which at least 3 amino acid residues of each of the heavy chain FR3 and the light chain FR are amino acid residues other than arginine residues and lysine residues, and at least 3 amino acid residues of the heavy chain FR3 include at least 3 selected from the amino acid residues at positions 68, 70, 72, 74, 75, 77, 79, 81, 82A, 82B, 83, 84, 85 and 87 of the heavy chain as defined by the Kabat method, and at least 3 amino acid residues of the light chain FR include at least 3 selected from the amino acid residues at positions 1, 3, 5, 7, 9, 10, 12, 14, 17, 18, 20, 22, 60, 63, 65, 67, 69, 70, 72, 74, 76, 77, 79 and 81 of the heavy chain as defined by the Kabat method.

In one embodiment, the method for producing an antibody includes: generating an antibody in which at least 3 amino acid residues of the heavy chain FR3 as defined by the Kabat method are arginine residues or lysine residues and at least 3 amino acid residues of the light chain FR3 as defined by the Kabat method are arginine residues or lysine residues; and recovering the antibody generated in the generating, in which affinity of the recovered antibody for an antigen is higher than affinity of an antibody in which at least 3 amino acid residues of each of the heavy chain FR3 and the light chain FR are amino acid residues other than arginine residues and lysine residues, and at least 3 amino acid residues of the heavy chain FR3 include at least 3 selected from the amino acid residues at positions 68, 70, 72, 74, 75, 77, 79, 81, 82A, 82B, 83, 84, 85 and 87 of the heavy chain as defined by the Kabat method, and at least 3 amino acid residues of the light chain FR include at least 3 selected from the amino acid residues at positions 60, 63, 65, 67, 69, 70, 72, 74, 76, 77, 79 and 81 of the heavy chain as defined by the Kabat method.

In one embodiment, at least 3 amino acid residues that are arginine residues or lysine residues in each of the heavy chain FR3 and the light chain FR3 of the generated antibody may be, for example, any of 7) to 12) described above.

In the production method of the present embodiment, the antibody can be generated by known DNA recombination technology, other molecular biological techniques, and the like. For example, first, a polynucleotide encoding an amino acid sequence of the antibody of the present embodiment is prepared from a polynucleotide encoding an amino acid sequence of any antibody. Then, the antibody of the present embodiment is generated by a protein expression system using the prepared polynucleotide. The protein expression system is the same as that described for the method of the present embodiment above.

The polynucleotide encoding the amino acid sequence of the antibody of the present embodiment can be prepared, for example, as follows, as described in the method of the present embodiment above. RNA extracted from a hybridoma that produces any antibody is used to synthesize a polynucleotide encoding the heavy chain and a polynucleotide encoding the light chain of the antibody, by a reverse transcription reaction and a RACE method. The polynucleotide encoding the heavy chain as a template is amplified by PCR using a primer for changing at least 3 amino acid residues of heavy chain FR3 to arginine residues or lysine residues. Thereby, a polynucleotide encoding the amino acid sequence of the heavy chain of the antibody of the present embodiment can be obtained. By incorporating the obtained polynucleotide and the polynucleotide encoding the light chain of any antibody described above into an expression vector, an expression vector containing a polynucleotide encoding the antibody of the present embodiment can be obtained.

In the antibody of the present embodiment, when at least 3 amino acid residues of each of the heavy chain FR3 and the light chain FR are arginine residues or lysine residues, the same procedure as in the preparation of the polynucleotide encoding the heavy chain may be carried out. That is, in the production method of the present embodiment, a polynucleotide encoding the light chain of any antibody as a template is amplified by PCR using a primer for changing at least 3 amino acid residues of the light chain FR to arginine residues or lysine residues, thereby a polynucleotide encoding the light chain of the present embodiment can be obtained.

In the production method of the present embodiment, by transforming or transfecting the expression vector containing a polynucleotide encoding the antibody of the present embodiment into an appropriate host cell, the antibody of the present embodiment can be generated in the host cell. Alternatively, the antibody of the present embodiment can be generated by adding a polynucleotide encoding the antibody of the present embodiment to a cell-free protein synthesis system and performing a synthesis reaction.

In the production method of the present embodiment, the antibody of the present embodiment can be obtained by recovering the generated antibody from the protein expression system. The method of recovering the antibody is the same as that described for the method of the present embodiment above. If necessary, the recovered antibody may be purified by a known method such as gel filtration.

Hereinbelow, the present invention will be described in detail by examples, but the present invention is not limited to these examples.

EXAMPLES

Example 1

Preparation of Antibody in Which Amino Acid Residue of Heavy Chain FR3 is Modified By substituting 3 amino acid residues of heavy chain FR3 of an anti-lysozyme antibody with arginine residues, 68, 70

72 variant, 79, 81, 82A variant, and 82B, 83, 84 variant were prepared as modified antibodies of the anti-lysozyme antibody.

(1) Obtainment of Gene of Wild-Type Anti-Lysozyme Antibody

A gene of a mouse anti-lysozyme antibody (HyHEL-10) was synthesized by GenScript Japan Inc. on commission, so that a plasmid DNA containing a gene of a wild-type anti-lysozyme antibody was obtained.

(2) Preparation of Variant of Anti-Lysozyme Antibody
[Reagents]
 QIAprep Spin Miniprep kit (QIAGEN)
 PrimeSTAR (registered trademark) Max DNA Polymerase (Takara Bio Inc.)
 Ligation high ver.2 (TOYOBO CO., LTD.)
 T4 Polynucleotide Kinase (TOYOBO CO., LTD.)
 Dpn I (TOYOBO CO., LTD.)
 Competent high DH5α (TOYOBO CO., LTD.)
(2.1) Primer Design and PCR Based on a base sequence of the wild-type anti-lysozyme antibody gene in the plasmid DNA obtained in the above (1), a primer set for obtaining a polynucleotide encoding a light chain and a primer set for obtaining a polynucleotide encoding a heavy chain in which the following 3 amino acid residues in FR3 were substituted with arginine residues were designed.
 Amino acid residues at positions 68, 70 and 72 of the heavy chain as defined by the Kabat method;
 Amino acid residues at positions 79, 81 and 82A of the heavy chain as defined by the Kabat method; and
 Amino acid residues at positions 82B, 83 and 84 of the heavy chain as defined by the Kabat method.

Using the plasmid DNA obtained in the above (1) as a template, a PCR reaction solution with the following composition was prepared.
[PCR Reaction Solution]

| PrimeSTAR (registered trademark) Max DNA Polymerase | 12.5 μL |
| --- | --- |
| Forward primer (10 μM) | 1 μL |
| Reverse primer (10 μM) | 1 μL |
| Template plasmid (3 ng/μL) | 1 μL |
| Purified water | 9.5 μL |
| Total | 25 μL |

The prepared PCR reaction solution was subjected to a PCR reaction under the following reaction conditions.
[Reaction Conditions]

30 cycles at 98° C. for 10 seconds, 98° C. for 10 seconds, 54° C. for 10 seconds and 72° C. for 45 seconds, and at 72° C. for 3 minutes.

The obtained PCR product was fragmented by adding 1 μL of DpnI (10 U/μL) to the PCR product (25 μL). Using the DpnI-treated PCR product, a ligation reaction solution with the following composition was prepared. The reaction solution was incubated at 16° C. for 1 hour to perform a ligation reaction.
[Ligation Reaction Liquid]

| DpnI-treated PCR product | 2 μL |
| --- | --- |
| Ligation high ver. 2 | 5 μL |
| T4 Polynucleotide kinase | 1 μL |
| Purified water | 7 μL |
| Total | 15 μL |

(2.2) Transformation, Plasmid Extraction and Sequence Confirmation

The solution (3 μL) after the ligation reaction was added to DH5α (30 μL), and the mixture was allowed to stand on ice for 30 minutes. Thereafter, the mixture was heat shocked by heating at 42° C. for 45 seconds. The mixture was again allowed to stand on ice for 2 minutes, then the whole amount was applied to an ampicillin-containing LB plate. The plate was incubated at 37° C. for 16 hours to obtain *E. coli* transformants. Single colonies on the plate were placed in the ampicillin-containing LB liquid medium, and the medium was shake-cultured (250 rpm) at 37° C. for 16 hours. Plasmids DNA were extracted from the obtained *E. coli* using the QIAprep Spin Miniprep kit. The base sequence of each obtained plasmid DNA was confirmed using pCDNA 3.4 vector primer. Hereinafter, these plasmids DNA were used as plasmids DNA for expressing mammalian cells.

(3) Expression in Mammalian Cells
[Reagents]
 Expi293 (trademark) cells (Invitrogen)
 Expi293 (trademark) Expression medium (Invitrogen)
 ExpiFectamine (trademark) 293 transfection kit (Invitrogen)
(3.1) Transfection Expi293 cells were proliferated by shaking culture (125 rpm) at 37° C. in a 5% $CO_2$ atmosphere. 30 mL of cell culture ($3.0 \times 10^6$ cells/mL) was prepared according to the number of samples. A DNA solution with the following composition was prepared using a plasmid DNA encoding each variant and a plasmid DNA encoding a wild-type antibody. The DNA solution was allowed to stand for 5 minutes.
[DNA Solution]

| Light chain plasmid solution | Amount (μL) corresponding to 15 μg |
| --- | --- |
| Heavy chain plasmid solution | Amount (μL) corresponding to 15 μg |
| Onti-MEM (trademark) | Appropriate amount (mL) |
| Total | 1.5 mL |

A transfection reagent having the following composition was prepared. The transfection reagent was allowed to stand for 5 minutes.

| ExpiFectamine reagent | 80 μL |
| --- | --- |
| Opti-MEM (trademark) | 1420 μL |
| Total | 1.5 mL |

The prepared DNA solution and the transfection reagent were mixed. The mixture was allowed to stand for 20 minutes. The resulting mixture (3 mL) was added to the cell culture (30 mL). The mixture was shake-cultured (125 rpm) at 37° C. for 20 hours in a 5% $CO_2$ atmosphere. After 20 hours, 150 μL and 1.5 mL of ExpiFectamine (trademark) transfection enhancers 1 and 2 were added to each culture, respectively. Each mixture was shake-cultured (125 rpm) at 37° C. for 6 days in a 5% $CO_2$ atmosphere.

(3.2) Recovery and Purification of Antibody

Each cell culture was centrifuged at 3000 rpm for 15 minutes, and the culture supernatant was recovered. The culture supernatant contains each antibody secreted from transfected Expi293 (trademark) cells. The obtained culture supernatant was again centrifuged at 15000×G for 10 minutes, and the supernatant was recovered. To the obtained supernatant (30 mL) was added 100 μL of antibody purification carrier Ni Sepharose High Performance (GE Healthcare), and the mixture was reacted at room temperature for 2 hours. The carrier was recovered to remove the supernatant, and TBS (1 mL) was added to wash the carrier. To the carrier was added 1000 μL of TBS containing 100 mM imidazole to elute the antibody captured on the carrier. This elution operation was performed a total of 3 times to obtain an antibody solution.

Based on the base sequence of the wild-type anti-lysozyme antibody gene, amino acid sequences of a light chain and a heavy chain of the antibody (Fab) were determined. These amino acid sequences were as follows. The amino acid sequences of the heavy chains of each prepared variant (Fab) are also shown below. Underlined portion indicates an amino acid residue substituted from the wild-type amino acid sequence. In the amino acid sequence of the heavy chain, "CGGSHHHHHH" (SEQ ID NO: 25) at C terminus indicates an amino acid sequence of a His tag.

```
Light chain of wild-type anti-lysozyme antibody
(HyHEL-10)
                                        (SEQ ID NO: 12)
DIVLTQSPATLSVTPGNSVSLSCRASQSIGNNLHWYQQKSHESPRLLIKY

ASQSISGIPSRFSGSGSGTDFTLSINSVETEDFGMYFCQQSNSWPYTFGG

GTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC

Heavy chain of wild-type anti-lysozyme antibody
(HyHEL-10)
                                        (SEQ ID NO: 13)
DVQLQESGPSLVKPSQTLSLTCSVTGDSITSDYWSWIRKFPGNRLEYMG

YVSYSGSTYYNPSLKSRISITRDTSKNQYYLDLNSVTTEDTATYYCANWD

GDYWGQGTLVTVSAAKTTPPSVYPLAPGSAAQTNSMVTLGCLVKGYFPEP

VTVTWNSGSLSSGVHTFPAVLQSDLYTLSSSVTVPSSTWPSETVTCNVAH

PASSTKVDKKIVPRDCGSKPSICGGSHHHHHH

Heavy chain of 68, 70, 72 variant of anti-lysozyme
antibody
                                        (SEQ ID NO: 14)
DVQLQESGPSLVKPSQTLSLTCSVTGDSITSDYWSWIRKFPGNRLEYMG

YVSYSGSTYYNPSLKSRIRIRRRTSKNQYYLDLNSVTTEDTATYYCANWD

GDYWGQGTLVTVSAAKTTPPSVYPLAPGSAAQTNSMVTLGCLVKGYFPEP

VTVTWNSGSLSSGVHTFPAVLQSDLYTLSSSVTVPSSTWPSETVTCNVAH

PASSTKVDKKIVPRDCGSKPSICGGSHHHHHH

Heavy chain of 79, 81, 82A variant of anti-
lysozyme antibody
                                        (SEQ ID NO: 15)
DVQLQESGPSLVKPSQTLSLTCSVTGDSITSDYWSWIRKFPGNRLEYMG

YVSYSGSTYYNPSLKSRISITRDTSKNQYRLRLRSVTTEDTATYYCANWD

GDYWGQGTLVTVSAAKTTPPSVYPLAPGSAAQTNSMVTLGCLVKGYFPEP

VTVTWNSGSLSSGVHTFPAVLQSDLYTLSSSVTVPSSTWPSETVTCNVAH

PASSTKVDKKIVPRDCGSKPSICGGSHHHHHH

Heavy chain of 82B, 83, 84 variant of anti-
lysozyme antibody
                                        (SEQ ID NO: 16)
DVQLQESGPSLVKPSQTLSLTCSVTGDSITSDYWSWIRKFPGNRLEYMG

YVSYSGSTYYNPSLKSRISITRDTSKNQYYLDLNRVRREDTATYYCANWD

GDYWGQGTLVTVSAAKTTPPSVYPLAPGSAAQTNSMVTLGCLVKGYFPEP

VTVTWNSGSLSSGVHTFPAVLQSDLYTLSSSVTVPSSTWPSETVTCNVAH

PASSTKVDKKIVPRDCGSKPSICGGSHHHHHH
```

(4) Measurement of Affinity

Affinity of the prepared variants was measured using Biacore (registered trademark) 8K (GE Healthcare). Chicken egg white-derived lysozyme (Sigma-Aldrich) was used as an antigen for the anti-lysozyme antibody. Antigen was immobilized (immobilization: 50 RU) to a sensor chip for Biacore (registered trademark) Series S Sensor Chip CM5 (GE Healthcare). The antibody solution was diluted to prepare antibody solutions of 30 nM, 15 nM, 7.5 nM, 3.75 nM and 1.875 nM. The antibody solutions at each concentration were delivered to Biacore (registered trademark) 8K (GE Healthcare) (association time of 120 seconds and dissociation time of 1800 seconds). Measurement data was analyzed using Biacore (registered trademark) Evaluation software, and the data on the affinity of each antibody was obtained.

(5) Results $K_d$ values of each antibody are shown in Table 2. Logarithms of $K_d$ values of each antibody are shown in FIG. 1. As shown in Table 2 and FIG. 1, the $K_d$ values of the 68, 70, 72 variant, the 79, 81, 82A variant, and the 82B, 83, 84 variant in which the FR3 of the heavy chain was modified were lower than the $K_d$ value of the wild-type anti-lysozyme antibody. Therefore, these variants had improved affinity for an antigen as compared with the wild-type antibody, by substituting 3 amino acid residues of FR3 of the heavy chain with arginine residues.

TABLE 2

| Anti-lysozyme antibody | $K_d$ (M) |
| --- | --- |
| Wild type | 1.31E−10 |
| 68, 70, 72 Variant | 5.78E−11 |
| 79, 81, 82A Variant | 1.01E−10 |
| 82B, 83, 84 Variant | 8.91E−11 |

Reference Example

Analysis of Amino Acid Sequence of Heavy Chain FR3 of Anti-Lysozyme Antibody

In order to find features common to the variants of Example 1 with improved affinity for an antigen, the present inventors calculated amino acid frequencies at each position of FR3 of the heavy chain. The present inventors considered that a side chain of the amino acid residue facing the surface of the antibody molecule is involved in the improvement in affinity for an antigen, and calculated ratios of solvent-exposed surface areas of each amino acid residue of FR3 of the heavy chain.

(1) Amino Acid Frequency

Amino acid sequences of heavy chains of about 30,000 mouse antibodies were downloaded as reference antibodies from public database abYsis. The obtained amino acid sequences of heavy chains of reference antibodies were aligned so that the numbers of the amino acid residues in FR3 of the heavy chains assigned by Kabat method matched. Amino acid frequencies at each position of FR3 of the obtained heavy chains of reference antibodies were obtained. Sequence alignment and amino acid frequencies were obtained by abYsis. It was found that appearance frequencies of serine (S), threonine (T), aspartic acid (D) and glutamic acid (E) tended to be high at positions corresponding to the amino acid residues modified in the variants of Example 1. Therefore, the sum of amino acid frequencies of S, T, D and E at each position of FR3s of the heavy chains was calculated by the following formula (II). In the formula (II), in the aligned amino acid sequences of heavy chains of a plurality of reference antibodies, the sum of amino acid frequencies at one position (X (%)) is calculated from the numbers of S, T, D and E appearing at the position and the number of the obtained amino acid sequences of heavy chains of reference antibodies. The obtained numbers by the Kabat method assigned to FR3s of heavy chains of reference antibodies were the same for FR3 of a heavy chain of a wild-type anti-lysozyme antibody. Therefore, the sum of amino acid frequencies obtained from the amino acid sequences of heavy chains of reference antibodies was used as a value for the amino acid sequence of a heavy chain of a wild-type anti-lysozyme antibody.

[Expression 1]

$$X\ (\%) = \frac{(\text{Number of } S) + (\text{Number of } T) + (\text{Number of } D) + (\text{Number of } E)}{(\text{Number of amino acid sequences of heavy chains of reference antibodies})} \times 100 \quad (II)$$

(2) Ratio of Solvent-Exposed Surface Area

An amino acid sequence of a heavy chain of a wild-type anti-lysozyme antibody was retrieved from PDB, a public database that provides three-dimensional structure data of proteins, and three-dimensional structure data of a heavy chain of the antibody was downloaded. Using the obtained three-dimensional structure data, ratios of solvent-exposed surface areas of each amino acid residue of FR3 of a heavy chain of a wild-type anti-lysozyme antibody were obtained by Discovery Studio Client v17.2.0.16349. In Discovery Studio Client v17.2.0.16349, the ratios of solvent-exposed surface area (Y (%)) were calculated by the following formula (III). In the formula, "Ala-X-Ala" is a tripeptide consisting of a sequence in which the amino acid X is sandwiched between two alanines.

[Expression 2]

$$Y\ (\%) = \frac{(\text{Solvent-exposed surface area of amino acid } X \text{ in protein})}{(\text{Solvent-exposed surface area of amino acid } X \text{ in Ala-}X\text{-Ala})} \times 100 \quad (III)$$

(3) Results

First, in Example 1, the amino acid residue to be substituted with an arginine residue was selected from amino acid residues other than a vernier zone residue in the heavy chain FR3 of the wild-type anti-lysozyme antibody. From the above (1), the amino acid residue substituted with an arginine residue in Example 1 was an amino acid residue at a position where the sum of amino acid frequencies of S, T, D and E in the amino acid sequence of heavy chain FR3 of the wild-type anti-lysozyme antibody was 15% or more. From the above (2), the amino acid residue substituted with an arginine residue in Example 1 was an amino acid residue at a position where the ratio of solvent-exposed surface area was 10% or more in the amino acid sequence of heavy chain FR3 of the wild-type anti-lysozyme antibody. Therefore, as a feature common to the variants of Example 1, it was found that 3 of the amino acid residues satisfying all the following conditions (a), (b) and (c) were substituted with arginine residues.

(a) in the amino acid sequence of heavy chain FR3, being amino acid residues other than a vernier zone residue;

(b) in the amino acid sequence of heavy chain FR3, being present at positions such that the sum of amino acid frequencies of S, T, D and E and glutamic acid (E) is 15% or more; and (c) in the amino acid sequence of heavy chain FR3, being amino acid residues showing a ratio of solvent-exposed surface area of 10% or more.

In the amino acid sequence of heavy chain FR3 of the mouse anti-lysozyme antibody, the amino acid residues having the features of the above (a), (b), and (c) were found to be amino acid residues at positions 68, 70, 72, 74, 75, 77, 79, 81, 82A, 82B, 83, 84, 85 and 87 of the heavy chain as defined by the Kabat method.

Example 2

Preparation of Antibody in Which Amino Acid Residue of Heavy Chain FR3 is Modified (2)

In an antibody other than the anti-lysozyme antibody, whether affinity for an antigen is improved by substituting 3 of the amino acid residues satisfying all the above conditions (a), (b) and (c) with arginine residues or lysine residues was verified. Specifically, variants of a humanized anti-HER2 antibody (trastuzumab) and a mouse anti-human insulin antibody were prepared, and affinity of these variants for an antigen was measured.

(1) Obtainment of Gene of Each Antibody

A gene of a humanized anti-HER2 monoclonal antibody (trastuzumab) was synthesized by GenScript Japan Inc. on commission, so that a plasmid DNA containing the gene of the humanized anti-HER2 antibody was obtained. Plasmid DNA containing a gene of a mouse anti-human insulin antibody was obtained by the same method described in U.S. Patent Application Publication No. 2018/0179298.

(2) Preparation of Variants (2.1) Analysis of Amino Acid Sequence of Heavy Chain FR3 of Humanized Anti-HER2 Antibody Amino acid sequences of heavy chains of about 30,000 human antibodies were downloaded as reference antibodies from database abYsis. In the same manner as in Reference Example, the obtained amino acid sequences of heavy chains of reference antibodies were aligned, and the sum of amino acid frequencies of S, T, D and E at each position of the amino acid sequence of heavy chain FR3 was calculated. The ratio of solvent-exposed surface area of each amino acid residue of heavy chain FR of the humanized anti-HER2 antibody was obtained based on three-dimensional structure data of a heavy chain of a humanized anti-HER2 antibody downloaded from the database PDB in the same manner as in Reference Example. Also in the humanized anti-HER2 antibody, the amino acid residues having the features of the above (a), (b) and (c) were the amino acid residues at positions 68, 70, 72, 74, 75, 77, 79, 81, 82A, 82B, 83, 84, 85 and 87 of the heavy chain as defined by the Kabat method.

(2.2) Analysis of Amino Acid Sequence of Heavy Chain FR3 of Mouse Anti-Human Insulin Antibody As the sum of amino acid frequencies of S, T, D and E at each position of the amino acid sequence of heavy chain FR3, the data for the mouse anti-lysozyme antibody obtained in Reference Example was used. The ratio of solvent-exposed surface area of each amino acid residue of heavy chain FR of a mouse anti-human insulin antibody was calculated using modeling structure data obtained by simulation based on amino acid sequence information of the anti-insulin antibody and three-dimensional structure data of a known mouse antibody. Modeling was performed using Discovery Studio. Also in the mouse anti-insulin antibody, the amino acid residues having the features of the above (a), (b) and (c) were the amino acid residues at positions 68, 70, 72, 74, 75, 77, 79, 81, 82A, 82B, 83, 84, 85 and 87 of the heavy chain as defined by the Kabat method.

(2.3) Obtainment of Gene Encoding Heavy Chain of Variant of Antibody

Based on a base sequence of the humanized anti-HER2 antibody gene in the plasmid DNA obtained in the above (1), a primer set for obtaining a polynucleotide encoding a light chain and a primer set for obtaining a polynucleotide encoding a heavy chain in which the following 3 amino acid residues in FR3 were substituted with arginine residues were designed. Based on a base sequence of the mouse anti-insulin antibody gene in the plasmid DNA obtained in the above (1), a primer set for obtaining a polynucleotide encoding a light chain and a primer set for obtaining a polynucleotide encoding a heavy chain in which the following 3 amino acid residues in FR3 were substituted with arginine residues or lysine residues were designed. PCR was performed in the same manner as in Example 1 using these primer sets.

Amino acid residues at positions 68, 70 and 72 of the heavy chain as defined by the Kabat method;
Amino acid residues at positions 72, 77 and 79 of the heavy chain as defined by the Kabat method;
Amino acid residues at positions 74, 75 and 77 of the heavy chain as defined by the Kabat method;
Amino acid residues at positions 79, 81 and 82A of the heavy chain as defined by the Kabat method;
Amino acid residues at positions 82B, 83 and 84 of the heavy chain as defined by the Kabat method; and
Amino acid residues at positions 84, 85 and 87 of the heavy chain as defined by the Kabat method.

Using the obtained PCR product, a plasmid containing a gene encoding a heavy chain of variant and a plasmid containing a gene encoding a wild-type light chain were obtained in the same manner as in Example 1. Using these plasmids, each antibody was expressed in Expi293 (trademark) cells in the same manner as in Example 1. The obtained culture supernatant was purified to obtain solutions of variants of the anti-HER2 antibody and the anti-insulin antibody.

Based on the base sequence of the wild-type humanized anti-HER2 antibody gene, amino acid sequences of a light chain and a heavy chain of the antibody (Fab) were determined. These amino acid sequences were as follows. The amino acid sequences of the heavy chains of each prepared variant (Fab) are also shown below. Underlined portion indicates an amino acid residue substituted from the wild-type amino acid sequence.

```
Light chain of wild-type humanized anti-HER2
antibody (trastuzumab)
                                      (SEQ ID NO: 17)
DIQMTQSPSSLSASVGDRVTITCRASQDVNTAVAWYQQKPGKAPKLLI

YSASFLYSGVPSRFSGSRSGTDFTLTISSLQPEDFATYYCQQHYTTPPTF

GQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTH

QGLSSPVTKSFNRGEC

Heavy chain of wild-type humanized anti-HER2
antibody (trastuzumab)
                                      (SEQ ID NO: 18)
EVQLVESGGGLVQPGGSLRLSCAASGFNIKDTYIHWVRQAPGKGLEW

VARTYPTNGYTRYADSVKGRFTISADTSKNTAYLQMNSLRAEDTAVYYCS

RWGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPPKSCDKTGSCGGHHHHHH

Heavy chain of 68, 70, 72 variant of humanized
anti-HER2 antibody
                                      (SEQ ID NO: 19)
EVQLVESGGGLVQPGGSLRLSCAASGFNIKDTYIHWVRQAPGKGLEW

VARTYPTNGYTRYADSVKGRFRIRARTSKNTAYLQMNSLRAEDTAVYYCS

RWGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPPKSCDKTGSCGGHHHHHH

Heavy chain of 72, 77, 79 variant of humanized
anti-HER2 antibody
                                      (SEQ ID NO: 20)
EVQLVESGGGLVQPGGSLRLSCAASGFNIKDTYIHWVRQAPGKGLEW

VARIYPTNGYTRYADSVKGRFTISARTSKNRARLQMNSLRAEDTAVYYCS

RWGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPPKSCDKTGSCGGHHHHHH

Heavy chain of 74, 75, 77 variant of humanized
anti-HER2 antibody
                                      (SEQ ID NO: 21)
EVQLVESGGGLVQPGGSLRLSCAASGFNIKDTYIHWVRQAPGKGLEW

VARIYPTNGYTRYADSVKGRFTISADTRRNRAYLQMNSLRAEDTAVYYCS

RWGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPPKSCDKTGSCGGHHHHHH

Heavy chain of 79, 81, 82A variant of humanized
anti-HER2 antibody
                                      (SEQ ID NO: 22)
EVQLVESGGGLVQPGGSLRLSCAASGFNIKDTYIHWVRQAPGKGLEW

VARIYPTNGYTRYADSVKGRFTISADTSKNTARLRMRSLRAEDTAVYYCS

RWGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPPKSCDKTGSCGGHHHHHH
```

-continued

Heavy chain of 82B, 83, 84 variant of humanized
anti-HER2 antibody
(SEQ ID NO: 23)
EVQLVESGGGLVQPGGSLRLSCAASGFNIKDTYIHWVRQAPGKGLEW

VARIYPTNGYTRYADSVKGRFTISADTSKNTAYLQMNRLRREDTAVYYCS

RWGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPPKSCDKTGSCGGHHHHHH

Heavy chain of 84, 85, 87 variant of humanized
anti-HER2 antibody
(SEQ ID NO: 24)
EVQLVESGGGLVQPGGSLRLSCAASGFNIKDTYIHWVRQAPGKGLEW

VARIYPTNGYTRYADSVKGRFTISADTSKNTAYLQMNSLRRRDRAVYYCS

RWGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPPKSCDKTGSCGGHHHHHH (3) Measurement of Affinity

Figure 2:
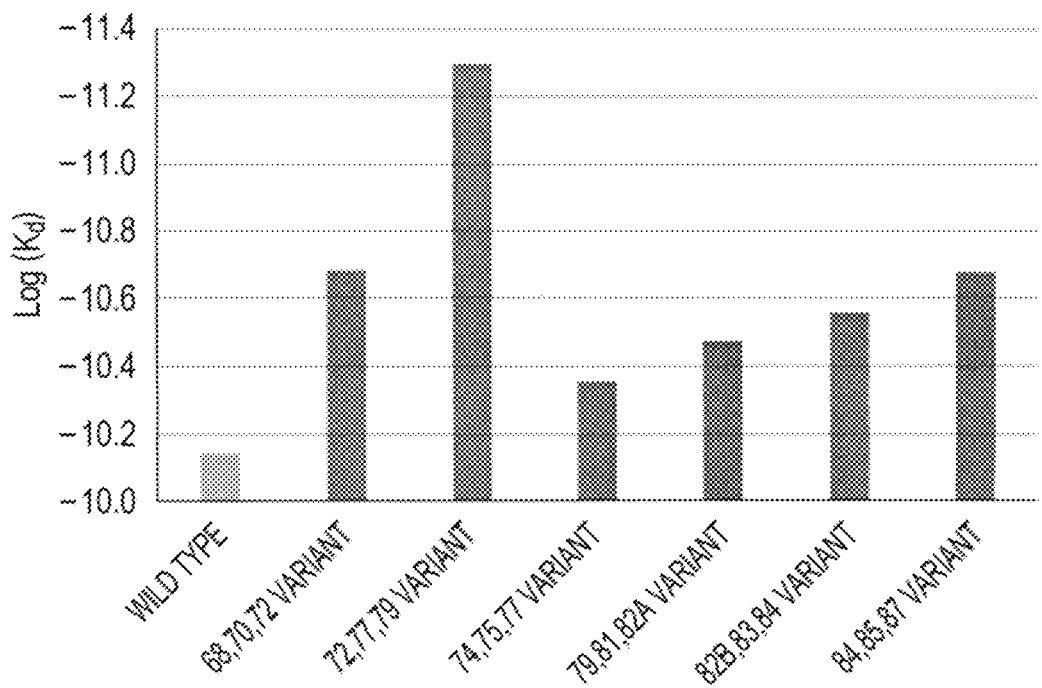
FIG. 2 is a graph showing affinity (logarithm of $K_d$ value) of a wild-type humanized anti-HER2 antibody and its variants for an antigen.
Figure 3:
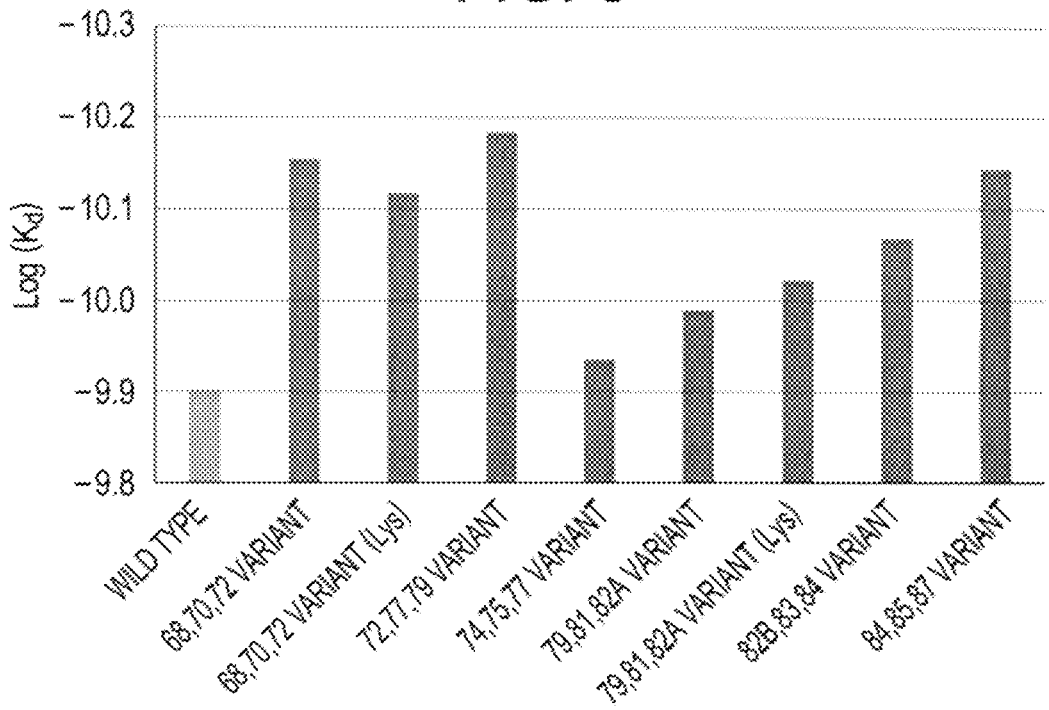
FIG. 3 is a graph showing affinity (logarithm of $K_d$ value) of a wild-type anti-insulin antibody and its variants for an antigen.

Affinity of the prepared variants was measured using Biacore (registered trademark) 8K (GE Healthcare) in the same manner as in Example 1. $K_d$ values of each antibody are shown in Tables 3 and 4. Logarithms of $K_d$ values of each antibody are shown in FIGS. 2 and 3. In Table 4, "68, 70, 72 variant (Lys)" and "79, 81, 82A variant (Lys)" are variants in which 3 amino acid residues in heavy chain FR3 of the anti-insulin antibody are substituted with lysine residues.

TABLE 3

| Anti-HER2 antibody | $K_d$ (M) |
|---|---|
| Wild type | 7.18E−11 |
| 68, 70, 72 Variant | 2.08E−11 |
| 72, 77, 79 Variant | 5.05E−12 |
| 74, 75, 77 Variant | 4.43E−11 |
| 79, 81, 82A Variant | 3.38E−11 |
| 82B, 83, 84 Variant | 2.78E−11 |
| 84, 85, 87 Variant | 2.11E−11 |

TABLE 4

| Anti-insulin antibody | $K_d$ (M) |
|---|---|
| Wild type | 1.25E−10 |
| 68, 70, 72 Variant | 7.01E−11 |
| 68, 70, 72 Variant (Lys) | 7.64E−11 |
| 72, 77, 79 Variant | 6.56E−11 |
| 74, 75, 77 Variant | 1.16E−10 |
| 79, 81, 82A Variant | 1.03E−10 |
| 79, 81, 82A Variant (Lys) | 9.50E−11 |
| 82B, 83, 84 Variant | 8.56E−11 |
| 84, 85, 87 Variant | 7.19E−11 |

(4) Results

As shown in Tables 3 and 4 and FIGS. 2 and 3, the Kd values of all the variants were lower than the Kd value of the wild-type antibody. Therefore, it was suggested that even for antibodies other than the anti-lysozyme antibody, affinity for an antigen can be improved by substituting 3 of the amino acid residues satisfying all the above conditions (a), (b) and (c) with arginine residues or lysine residues.

Example 3

Preparation of Antibody in Which Both Light Chain FR3 and Heavy Chain FR3 Are Modified In the variant in which heavy chain FR3 was modified, light chain FR3 was further modified to prepare a variant in which both the light chain FR3 and the heavy chain FR3 were modified. Whether affinity of this variant for an antigen was further improved as compared with that a variant in which only the heavy chain FR3 was modified was verified.

(1) Preparation of Variants

Based on a base sequence of the gene of the humanized anti-HER2 antibody obtained in Example 2, a primer set for obtaining a polynucleotide encoding a light chain in which amino acid residues at positions 63, 65 and 67 of the light chain FR3 as defined by the Kabat method were substituted with arginine residues was designed. PCR was performed in the same manner as in Example 1 using this primer set. Using the obtained PCR product, a plasmid containing a gene encoding a light chain in which the amino acid residues at positions 63, 65 and 67 of the light chain FR3 were substituted with arginine residues was obtained in the same manner as in Example 1. As a plasmid containing a gene encoding the heavy chain of the humanized anti-HER2 antibody, a plasmid containing a gene encoding the heavy chains of 72, 77, 79 variant and 82B, 83, 84 variant obtained in Example 2 was used. Using these plasmids, each antibody was expressed in Expi293 (trademark) cells in the same manner as in Example 1. The obtained culture supernatant was purified to obtain solutions of "light chain 63, 65, 67/heavy chain 72, 77, 79 variant" and "light chain 63, 65, 67/heavy chain 82B, 83, 84 variant" as variants of the anti-HER2 antibody in which mutations were introduced into both the light chain and the heavy chain.

(2) Measurement of Affinity

Figure 4:
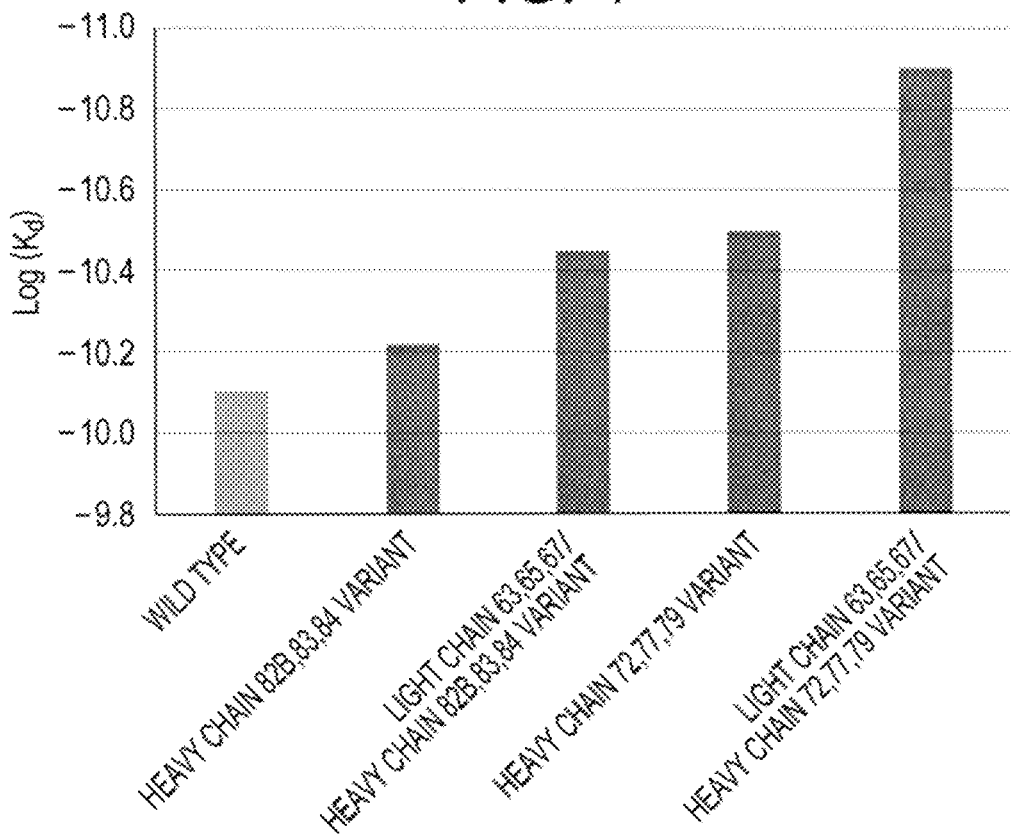
FIG. 4 is a graph showing affinity (logarithm of $K_d$ value) of a wild-type humanized anti-HER2 antibody and its variants for an antigen.

Affinity of the prepared variants was measured using Biacore (registered trademark) 8K (GE Healthcare) in the same manner as in Example 1. For comparison, affinity of the wild-type humanized anti-HER2 antibody, and the 72, 77, 79 variant and 82B, 83, 84 variant of Example 2 was also measured. $K_d$ values of each antibody are shown in Table 5. Logarithms of $K_d$ values of each antibody are shown in FIG. 4.

TABLE 5

| Anti-HER2 antibody | $K_d$ (M) |
|---|---|
| Wild type | 7.84E−11 |
| Heavy chain 82B, 83, 84 variant | 6.06E−11 |
| Light chain 63, 65, 67/heavy chain 82B, 83, 84 variant | 3.57E−11 |
| Heavy chain 72, 77, 79 variant | 3.21E−11 |
| Light chain 63, 65, 67/heavy chain 72, 77, 79 variant | 1.26E−11 |

(4) Results

As shown in Table 5 and FIG. 4, the Kd values of all the variants were lower than the Kd value of the wild-type antibody. The Kd value of the light chain 63, 65, 67/heavy chain 72, 77, 79 variant was lower than the Kd value of the heavy chain 72, 77, 79 variant in which only the heavy chain FR3 was modified. Similarly, the Kd value of the light chain 63, 65, 67/heavy chain 82B, 83, 84 variant was lower than the Kd value of the heavy chain 82B, 83, 84 variant in which only the heavy chain FR3 was modified. Therefore, it was suggested that by modifying both the light chain FR3 and the heavy chain FR3 of the antibody, an antibody with improved affinity for an antigen as compared with an antibody in which only the heavy chain FR3 was modified is obtained.

Example 4

Thermal Stability of Modified Antibody

How thermal stability of each variant of the anti-HER2 antibody prepared in Example 2 changes as compared with that of the wild type was examined.

(1) Purification of Antibodies by Size Exclusion Chromatography (SEC)

A solution containing the wild-type humanized anti-HER2 antibody and the 82B, 83, 84 variant of the anti-HER2 antibody obtained in Example 2 was purified by SEC using AKTA (GE Healthcare). SEC conditions were as follows.

[SEC Conditions]
- Column: Superdex 200 increase 10/300 GL (GE Healthcare)
- Mobile phase: phosphate buffered saline (PBS)
- Flow rate: 0.75 mL/min
- Elution amount: 1 CV
- Column wash: 1 CV (2) Measurement of Modification Temperature (Tm) with Differential Scanning Calorimeter (DSC)

Fractions containing each antibody were diluted with PBS to prepare antibody-containing samples (final concentration 5 µM). Tm of each antibody was measured using MicroCal VP-Capillary DSC (Malvern Instruments Ltd). Measurement conditions were as follows.

Figure 5:
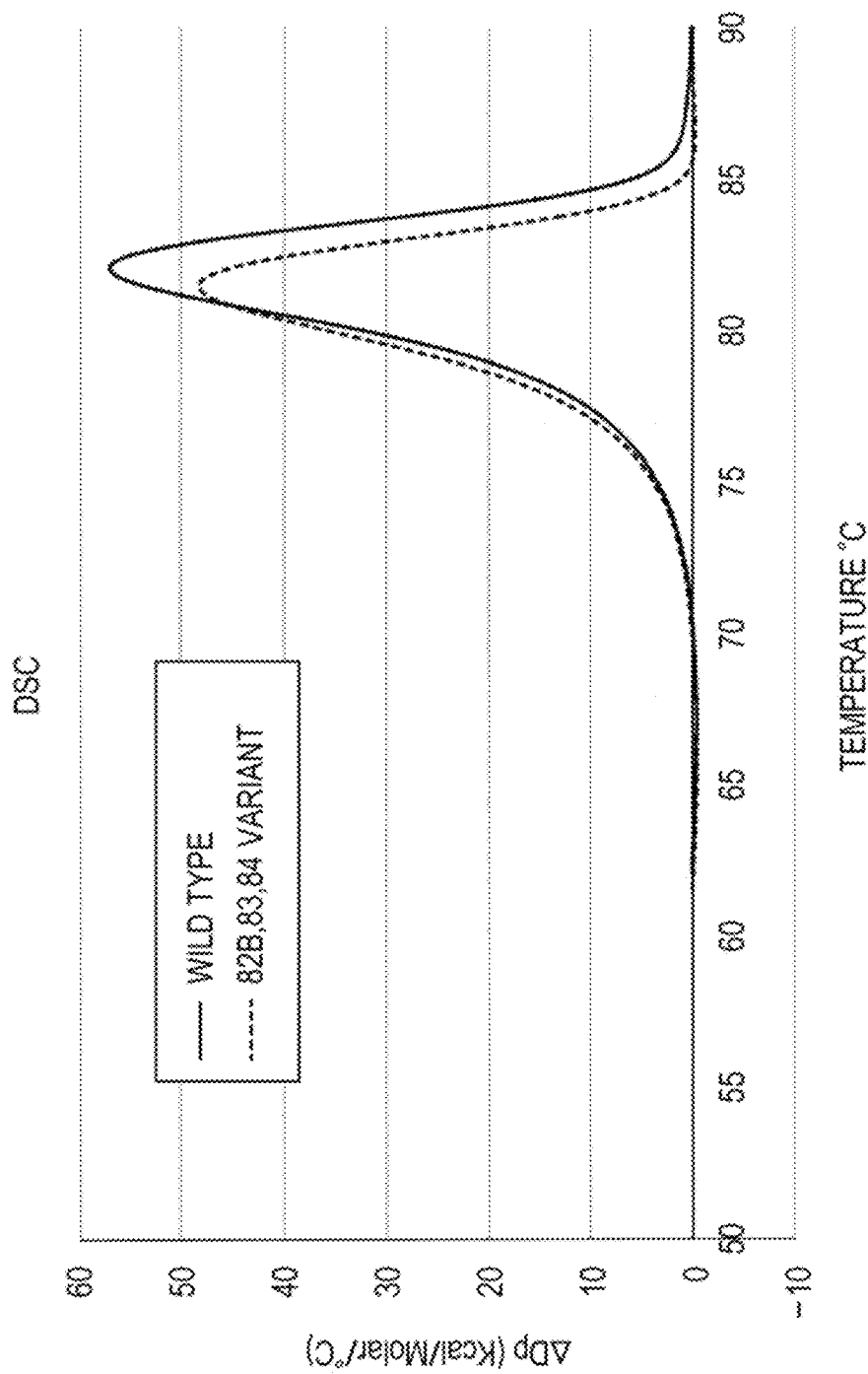
FIG. 5 is a graph showing results of measuring thermal stability of a wild-type humanized anti-HER2 antibody and its variant by a differential scanning calorimeter.

[DSC Measurement Conditions]
- Sample amount: 400 µL
- Measurement range: 30° C. to 90° C.
- Temperature elevation rate: 60° C./hr (3) Results Tm values and analytical peaks obtained by DSC measurement are shown in Table 6 and FIG. 5, respectively.

TABLE 6

| Anti-HER2 antibody | Tm (° C.) | Δ Tm (° C.) |
| --- | --- | --- |
| Wild type | 82.12 | — |
| 82B, 83, 84 Variant | 81.66 | −0.46 |

The 82B, 83, 84 variant of the anti-HER2 antibody had thermal stability reduced by 0.46° C. as compared with the wild-type antibody, but its reduction rate was less than 1%. The thermal stability of the humanized anti-HER2 antibody variants was found to be little changed from that of the wild-type antibody.

[Sequence Listing]

What is claimed is:

1. A method for improving affinity of an antibody for an antigen, the method comprising:

in an amino acid sequence of the antibody, changing at least 3 amino acid residues of framework region 3 (FR3) as defined by Kabat method to arginine residues or lysine residues, thereby improving affinity of the antibody for the antigen as compared with that of the antibody before said at least 3 amino acid residues are changed to arginine residues or lysine residues, wherein the antibody is a humanized anti-HER2 antibody comprising a heavy chain and a light chain, wherein said at least 3 amino acid residues comprise at least 3 selected from the group consisting of amino acid residues at positions 68, 70, 72, 74, 75, 77, 79, 81, 82A, 82B, 83, 84, 85 and 87 of the heavy chain as defined by the Kabat method, and wherein the antibody comprises light chain CDR1 of SEQ ID NO: 4, light chain CDR2 of SEQ ID NO: 5, light chain CDR3 of SEQ ID NO: 6, heavy chain CDR1 of SEQ ID NO: 8, heavy chain CDR2 of SEQ ID NO: 9 and heavy chain CDR3 of SEQ ID NO: 10.

2. The method according to claim 1, wherein said at least 3 amino acid residues in the antibody before changing are amino acid residues other than arginine residues and lysine residues.

3. The method according to claim 1, wherein said at least 3 amino acid residues are selected from the group consisting of the amino acid residues at positions 75, 77, 79, 81, 82A, 82B, 83, 84, 85 and 87 of the heavy chain as defined by the Kabat method.

4. The method according to claim 1, wherein the antibody is an antibody fragment.

5. The method according to claim 4, wherein the antibody fragment is Fab.

6. A method for producing an antibody, the method comprising:

generating the antibody in which at least 3 amino acid residues of framework region 3 (FR3) as defined by Kabat method are arginine residues or lysine residues; and recovering the antibody generated in the generating, wherein affinity of the recovered antibody for an antigen is higher than affinity of an antibody in which said at least 3 amino acid residues are amino acid residues other than arginine residues and lysine residues, wherein the antibody is a humanized anti-HER2 antibody comprising a heavy chain and a light chain, wherein the antibody comprises light chain CDR1 of SEQ ID NO: 4, light chain CDR2 of SEQ ID NO: 5, light chain CDR3 of SEQ ID NO: 6, heavy chain CDR1 of SEQ ID NO: 8, heavy chain CDR2 of SEQ ID NO: 9 and heavy chain CDR3 of SEQ ID NO: 10, and wherein said at least 3 amino acid residues comprise at least 3 selected from the group consisting of amino acid residues at positions 68, 70, 72, 74, 75, 77, 79, 81, 82A, 82B, 83, 84, 85 and 87 of the heavy chain as defined by the Kabat method.

7. The method according to claim 6, wherein the generating comprises changing said at least 3 amino acid residues from amino acid residues other than arginine residues and lysine residues to arginine residues or lysine residues.

8. The method according to claim 6, wherein, in the generating, the antibody is generated by a protein expression system using a polynucleotide encoding an amino acid sequence of the antibody.

9. The method according to claim 8, wherein, in the generating, the antibody is generated by a host cell into which an expression vector comprising the polynucleotide has been introduced.

10. The method according to claim 6, wherein said at least 3 amino acid residues are selected from the group consisting of the amino acid residues at positions 75, 77, 79, 81, 82A, 82B, 83, 84, 85 and 87 of athe heavy chain as defined by the Kabat method.

11. The method according to claim 6, wherein the antibody is an antibody fragment.

12. The method according to claim 11, wherein the antibody fragment is Fab.

13. The method according to claim 1, wherein the amino acid sequence of the antibody before changing said at least 3 amino acid residues comprises the amino acid sequence of SEQ ID NO: 11.

14. The method according to claim 1, wherein the light chain comprises an amino acid sequence of SEQ ID NO: 1 or SEQ ID NO:7.

15. The method according to claim 6, wherein the antibody comprises the amino acid sequence of SEQ ID NO: 11, excluding said at least 3 amino acid residues.

16. The method according to claim 6, wherein the light chain comprises the amino acid sequence of SEQ ID NO: 1 or SEQ ID NO:7.

17. The method according to claim 1, wherein the amino acid sequence of the antibody before changing said at least 3 amino acid residues comprises the amino acid sequence of SEQ ID NO: 3.

18. The method according to claim 6, wherein the antibody comprises the amino acid sequence of SEQ ID NO: 3, excluding said at least 3 amino acid residues.

19. The method according to claim 1, wherein the amino acid sequence of the antibody before changing said at least 3 amino acid residues comprises the amino acid sequence of SEQ ID NO: 2.

20. The method according to claim 6, wherein the antibody comprises the amino acid sequence of SEQ ID NO: 2, excluding said at least 3 amino acid residues.

* * * * *